(12) United States Patent
Worthington et al.

(10) Patent No.: US 7,110,345 B2
(45) Date of Patent: *Sep. 19, 2006

(54) MULTIPLE DATA LAYER OPTICAL DISCS FOR DETECTING ANALYTES

(75) Inventors: Mark O. Worthington, Irvine, CA (US); James R. Norton, Santa Ana, CA (US); Horacio Kido, Niland, CA (US); Victor M. Ortiz, Orange, CA (US)

(73) Assignees: Burstein Technologies, Inc., Irvine, CA (US); Nagaoka & Co., Ltd., Hyogo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/885,423

(22) Filed: Jul. 6, 2004

(65) Prior Publication Data
US 2005/0018583 A1    Jan. 27, 2005

Related U.S. Application Data

(63) Continuation of application No. 10/006,620, filed on Dec. 10, 2001, now Pat. No. 6,760,298.

(60) Provisional application No. 60/254,394, filed on Dec. 8, 2000, provisional application No. 60/255,233, filed on Dec. 12, 2000, provisional application No. 60/293,917, filed on May 24, 2001, provisional application No. 60/294,051, filed on May 29, 2001, provisional application No. 60/294,052, filed on May 29, 2001, provisional application No. 60/303,437, filed on Jul. 6, 2001, provisional application No. 60/306,226, filed on Jul. 18, 2001, provisional application No. 60/323,405, filed on Sep. 19, 2001.

(51) Int. Cl.
*G11B 7/24* (2006.01)
*G11B 5/09* (2006.01)

(52) U.S. Cl. .............. 369/275.1; 369/47.1; 369/53.1; 369/94

(58) Field of Classification Search ................ None
See application file for complete search history.

(56) References Cited

U.S. PATENT DOCUMENTS

| 3,555,284 A | 1/1971 | Norman |
| 3,736,432 A | 5/1973 | Sweet |
| 3,939,350 A | 2/1976 | Kronick et al. |

(Continued)

FOREIGN PATENT DOCUMENTS

EP          0 417 305 A1     6/1990

(Continued)

OTHER PUBLICATIONS

Tibbe et al., "Optical Tracking and Detection of Immunomagnetically Selected and Aligned Cells", Nature Biotechnology, vol. 17, Dec. 1999, pp. 1210-1213.

*Primary Examiner*—Muhammad Edun
(74) *Attorney, Agent, or Firm*—Knobbe, Martens, Olson & Bear, LLP.

(57) ABSTRACT

This invention relates to optical discs that preferably include multiple data layers and are configured to receive analytes which can be detected by an optical disc reader. The optical disc reader may be a standard optical disc reader or an optical disc reader modified therefrom. The optical disc may include (1) a first layer including optically readable structures which have encoded tracking information, and speed information enabling an optical disc reader to rotate the optical disc at a speed that is determinable from the speed information; (2) a second layer including optically readable structures; and (3) an analyte section capable of receiving an analyte which can be read by the optical disc reader.

34 Claims, 11 Drawing Sheets

U.S. PATENT DOCUMENTS

| | | |
|---|---|---|
| 3,966,322 A | 6/1976 | Greaves et al. |
| 4,608,344 A | 8/1986 | Carter et al. |
| 4,743,558 A | 5/1988 | Guigan |
| 4,870,508 A | 9/1989 | Van Rosmalen et al. |
| 4,898,832 A | 2/1990 | Klose et al. |
| 4,917,865 A | 4/1990 | Romanauskas |
| 4,961,916 A | 10/1990 | Lesage et al. |
| 5,002,867 A | 3/1991 | Macevicz |
| 5,021,236 A | 6/1991 | Gries et al. |
| 5,087,556 A | 2/1992 | Ertinghausen |
| 5,112,134 A | 5/1992 | Chow et al. |
| 5,281,540 A | 1/1994 | Merkh et al. |
| 5,310,523 A | 5/1994 | Smethers et al. |
| 5,329,461 A | 7/1994 | Allen et al. |
| 5,407,554 A | 4/1995 | Saurer |
| 5,413,939 A | 5/1995 | Gustafson et al. |
| 5,424,036 A | 6/1995 | Ushikubo |
| 5,478,750 A | 12/1995 | Bernstein et al. |
| 5,488,567 A | 1/1996 | Allen et al. |
| 5,492,806 A | 2/1996 | Drmanac et al. |
| 5,566,159 A | 10/1996 | Shapira |
| 5,585,069 A | 12/1996 | Zanzucchi et al. |
| 5,598,393 A | 1/1997 | Alon et al. |
| 5,631,166 A | 5/1997 | Jewell |
| 5,631,844 A | 5/1997 | Margrey et al. |
| 5,684,774 A | 11/1997 | Yamamuro |
| 5,700,655 A | 12/1997 | Croteau et al. |
| 5,736,410 A | 4/1998 | Zarling et al. |
| 5,834,758 A | 11/1998 | Trulson et al. |
| 5,874,219 A | 2/1999 | Rava et al. |
| 5,922,591 A | 7/1999 | Anderson et al. |
| 5,930,033 A | 7/1999 | Inoue et al. |
| 5,995,209 A | 11/1999 | Öhman et al. |
| 6,024,883 A | 2/2000 | Jewell |
| 6,026,068 A | 2/2000 | Obata et al. |
| 6,084,843 A | 7/2000 | Abe et al. |
| 6,121,048 A | 9/2000 | Zaffaroni et al. |
| 6,147,943 A | 11/2000 | Ogasawara et al. |
| 6,192,320 B1 | 2/2001 | Margrey et al. |
| 6,222,619 B1 | 4/2001 | Herron et al. |
| 6,225,625 B1 | 5/2001 | Pirrung et al. |
| 6,231,812 B1 | 5/2001 | Rothberg et al. |
| 6,277,653 B1 | 8/2001 | Challener et al. |
| 6,309,601 B1 | 10/2001 | Juncosa et al. |
| 6,327,031 B1 | 12/2001 | Gordon |
| 6,338,139 B1 | 1/2002 | Ando et al. |
| 6,387,331 B1 | 5/2002 | Hunter |
| 6,395,562 B1 | 5/2002 | Hammock et al. |
| 6,476,907 B1 | 11/2002 | Gordon |
| 6,560,546 B1 | 5/2003 | Shenk et al. |
| 6,760,298 B1 * | 7/2004 | Worthington et al. .... 369/275.1 |
| 2001/0052976 A1 | 12/2001 | Juncosa et al. |
| 2002/0097658 A1 | 7/2002 | Worthington et al. |
| 2002/0098528 A1 | 7/2002 | Gordon et al. |
| 2002/0106786 A1 | 8/2002 | Carvalho et al. |
| 2002/0139936 A1 | 10/2002 | Dumas |
| 2002/0163642 A1 | 11/2002 | Zoval et al. |

FOREIGN PATENT DOCUMENTS

| | | |
|---|---|---|
| EP | 0 392 475 A2 | 10/1990 |
| EP | 0 504 432 A1 | 9/1992 |
| EP | 0 521 421 A2 | 1/1993 |
| EP | 0 866 449 A2 | 9/1998 |
| WO | WO 96/09548 | 3/1996 |
| WO | WO 97/11460 | 3/1997 |
| WO | WO 97/21090 | 6/1997 |
| WO | WO 98/01858 | 1/1998 |
| WO | WO 98/12559 | 3/1998 |
| WO | WO 98/15356 | 4/1998 |
| WO | WO 99/32663 | 7/1999 |
| WO | WO 99/35499 | 7/1999 |
| WO | WO 00/20838 | 4/2000 |
| WO | WO 00/26677 | 5/2000 |
| WO | WO 02/06836 A2 | 1/2002 |

* cited by examiner

MULTIPLE DATA LAYER OPTICAL DISCS FOR DETECTING ANALYTES

RELATED APPLICATIONS

This application is a continuation of U.S. patent application No. 10/006,620 filed Dec. 10, 2001, now U.S. Pat. No. 6,760,298, issued on Jul. 6, 2004 which claims priority to U.S. Provisional Application Ser. No. 60/254,394, filed Dec. 8, 2000; U.S. Provisional Application Ser. No. 60/255,233, filed Dec. 12, 2000; U.S. Provisional Application Ser. No. 60/293,917, filed May 24, 2001; U.S. Provisional Application Ser. No. 60/294,051, filed May 29, 2001; U.S. Provisional Application Ser. No. 60/294,052, filed May 29, 2001; U.S. Provisional Application Ser. No. 60/303,437, filed Jul. 6, 2001; U.S. Provisional Application Ser. No. 60/306,226, filed Jul. 18, 2001; and U.S. Provisional Application Ser. No. 60/323,405, filed Sep. 19, 2001.

BACKGROUND OF THE INVENTION

1. Field of the Invention

This invention relates to optical discs that include multiple data layers and are configured to receive analytes which can be detected by an optical disc reader.

2. Description of the Related Art

Optical discs have been used for detection and characterization of biological and chemical samples. For instance, see WO 96/09548 (Gordon), EP A 392475 (Idemitsu), EP A 417 305 (Idemitsu), EP A 504432 (Idemitsu), and WO 98/12559 (Demers), all of which are incorporated herein by reference. Other examples of using optical discs to detect investigational samples can be found in U.S. Provisional Application 60/252,725, entitled "Optical Bio-Disc Including Microfluidic Circuit for Separation and Quantification of Agglutinated Microparticles or Cells and Methods Relating Thereto", U.S. Provisional Application No. 60/252,726, entitled "Bioactive Solid Phase for Specific Cell Capture and Optical Bio-Disc Including Same", and U.S. Provisional Application No. 60/257,705, entitled "Surface Assembly for Immobilizing DNA Capture Probes and Bead-Based Assay Including Optical Bio-Discs and Methods Relating Thereto" all of which are incorporated herein by reference.

Some of these previously described optical discs, however, are not designed to be read by standard optical disc readers, such as standard CD or DVD readers. For instance, the optical discs disclosed in EP A 392 475 (Idemitsu), EP A 417 305 (Idemitsu) and EP A 504 432 (Idemitsu) are not designed to be read by standard CD or DVD disc readers. The discs described in WO 96/09548 (Gordon) require the use of two optical detectors, one to detect the tracking information and the other to detect surface structures. In contrast, reading a standard CD or DVD needs only one optical detector.

Therefore, there is a need to design and manufacture an optical disc configured to receive an investigational sample that can be detected by a standard optical disc reader or an optical disc reader modified therefrom.

Over the past decade, scanning laser microscopy (SLM) has revolutionized life science imaging. However, SLM demands expensive and specialized optical equipment. Consequently, there exists a need to provide an inexpensive, generic device which can carry out laser scanning over microscopic specimens.

The present invention discovers that the minimum mechanical requirements for SLM, i.e. laser, focusing and detection optics, precision scanning means, and computer interface, may all be provided by a standard optical disc reader or an optical disc reader modified therefrom. Therefore, it is desirable to create an optical disc that can hold a microscopic sample that can be scanned by a standard optical disc reader. Such an optical disc presents a marked advantage over existing SLM technologies.

In order for a standard optical disc reader to operate an optical disc, the optical disc reader is typically required to be able to (1) accurately focus above the operational surface of the optical disc, (2) accurately follow the spiral track or utilize some form of uniform radial movement across the optical disc surface, (3) recover enough information to facilitate a form of speed control, such as CAV, CLV, CBR, or ZCLV, (4) maintain proper power control by logical information gathered from the optical disc or by signal patterns detected in the operational surface of the optical disc, and (5) respond to logic information that is used to control, for example, the position of the objective assembly, the speed of rotation, or the focusing position of the laser beam.

A typical optical disc system uses elements of the optical medium itself to satisfy at least some of these operational requirements. For instance, in a typical CD, the disc substrate is impressed with a spiral track made up of a series of embossed or impressed pits and lands. Light reflected from these pits and lands can be used to generate signals. These signals are used by the optical disc reader to maintain proper focusing and tracking. In a CD-R disc, a wobble groove is used to generate operational signals during disc recording. Dye marks are created during disc recording, and these dye marks may provide the requisite tracking structures during subsequent reading. Generally, under each of conventional optical disc standards, the structures that encode data may simultaneously serve to provide operational signals that enable an optical disc reader to operate the optical disc.

Conventional optical disc standards make no provision with respect to acquisition of information from investigational features, such as biological, chemical, or biochemical specimens, that are disposed on the disc. Investigational features disposed on the disc may disrupt the tracking of the disc. In addition, investigational structures or features may be sufficiently separated from operational structures, therefore preventing an optical disc reader from tracking the disc and detecting the investigational features concurrently and discriminably.

Therefore, there is a need to provide an optical disc that allows an optical disc reader to detect the investigational features without disrupting the tracking of the disc. There also exists a need to provide an optical disc that allows an optical disc reader to track the disc and read the investigational features concurrently and discriminably.

SUMMARY OF THE INVENTION

Therefore, it is an object of this invention to provide an optical disc configured to receive an analyte of interest that can be detected by an optical disc reader.

In accordance with one aspect of this invention, the optical disc includes (1) a first layer including optically readable structures which have encoded tracking information, and speed information enabling an optical disc reader to rotate the optical disc at a speed that is determinable from the speed information; (2) a second layer including optically readable structures; and (3) an analyte section capable of receiving an analyte which can be read by the optical disc reader. The analyte section may include a first chamber, and at least part of the first chamber is within the optical disc.

The optical disc may also include a channel which is located in at least one of the first layer and the second layer and which connects to the first chamber. The optical disc reader may be a DVD reader or a CD reader.

In one embodiment, the channel includes a valve that can be regulated by optically readable data encoded in the optical disc.

In another embodiment, the analyte section includes a second chamber, and at least part of the second chamber is within the optical disc. The optical disc may also include a channel which is located in at least one of the first layer and the second layer and which connects to the second chamber.

In accordance with another aspect of this invention, the optically readable structures in the first layer are impressed in a surface of the first layer and are coated with a first reflective layer, whereas the optically readable structures in the second layer are impressed in a surface of the second layer and are coated with a second reflective layer. The first reflective layer and the second reflective layer are located between the first layer and the second layer.

In one embodiment, at least one of the first and second reflective layers is semi-reflective.

In another embodiment, the first chamber includes a sample surface that is located within 15 micrometers from either the first data surface or the second data surface. The sample surface of the first chamber may hold the analyte.

In yet another embedment, at least one of the first data surface and the second data surface includes a cut-away area or window that lacks optical readable structures that have encoded tracking information. A surface of the first chamber may include the cut-away area or window. The cut-away area or window may lack reflective coatings.

In a preferred embodiment, the optically readable structures in the first layer or the optically readable structures in the second layer have encoded assay information for conducting an assay on the analyte.

In another preferred embodiment, the optically readable structures in the first layer or the optically readable structures in the second layer have encoded focus control information enabling the optical disc reader to move the focal point of a reading beam in a manner determinable from the focus control information.

In accordance with yet another aspect of this invention, at least one of the first layer and the second layer is a hologram. Preferably, at least part of an image plane of the hologram is located with the analyte section. The analyte section may include a surface that is located within 15 micrometers from the image plane of the hologram. The surface can hold the analyte. In one embodiment, the surface is within the image plane of the hologram.

In accordance with another aspect of this invention, a method is provided for the detection of the analyte held in the analyte section of the optical disc. The method includes: (1) providing the optical disc to the optical disc reader; (2) reading the optical disc; and (3) obtaining at least one signal which is indicative of the presence of the analyte.

In one embodiment, the optical disc reader includes at least two detectors, one detector being capable of generating tracking signals, and the other detector being capable of receiving radiation that passes through the optical disc and generating the signal which is indicative of the presence of the analyte.

BRIEF DESCRIPTION OF THE DRAWING FIGURES

Further aspects of the present invention together with additional features contributing thereto and advantages accruing therefrom will be apparent from the following description of the preferred embodiments of the invention which are shown in the accompanying drawing figures. It should be understood that all the drawings used herein are given by way of illustration, not limitation.

FIG. 1 demonstrates the functional components of an optical disc assembly according to one embodiment of the present invention.

Figure 15:
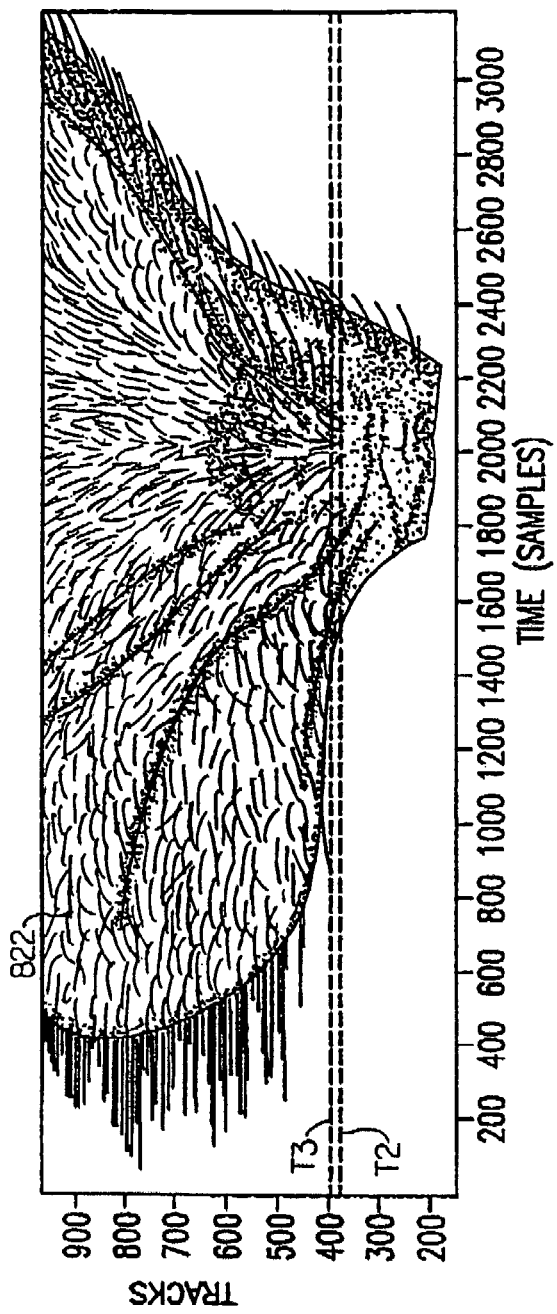
FIG. 15 illustrates the position of the gnat wing relative to the tracks of the operational structures.
Figure 16:
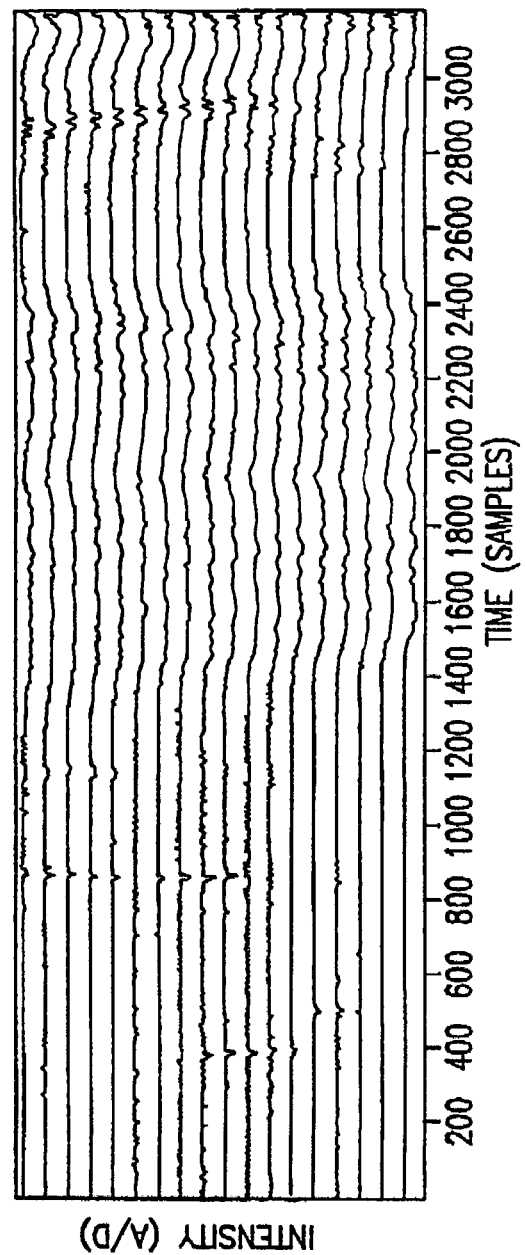

FIG. 16 demonstrates the HF signals acquired from a series of consecutive tracks of the operational structures represented in FIG. 15.

Figure 17:
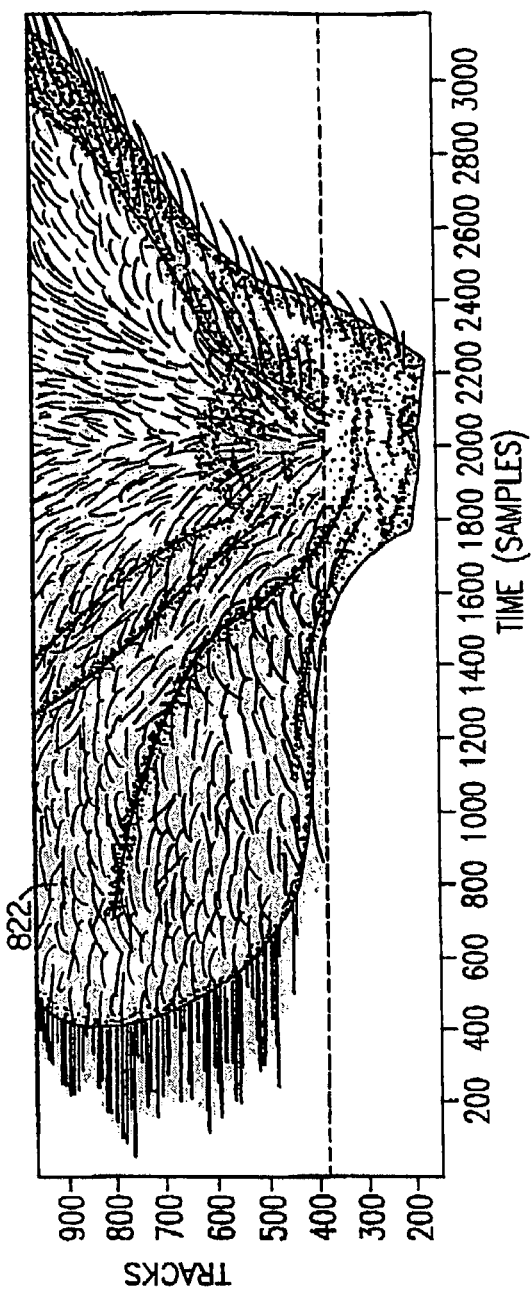

FIG. 17 depicts the position of the gnat wing relative to the tracks of the operational structures.

Figure 18:
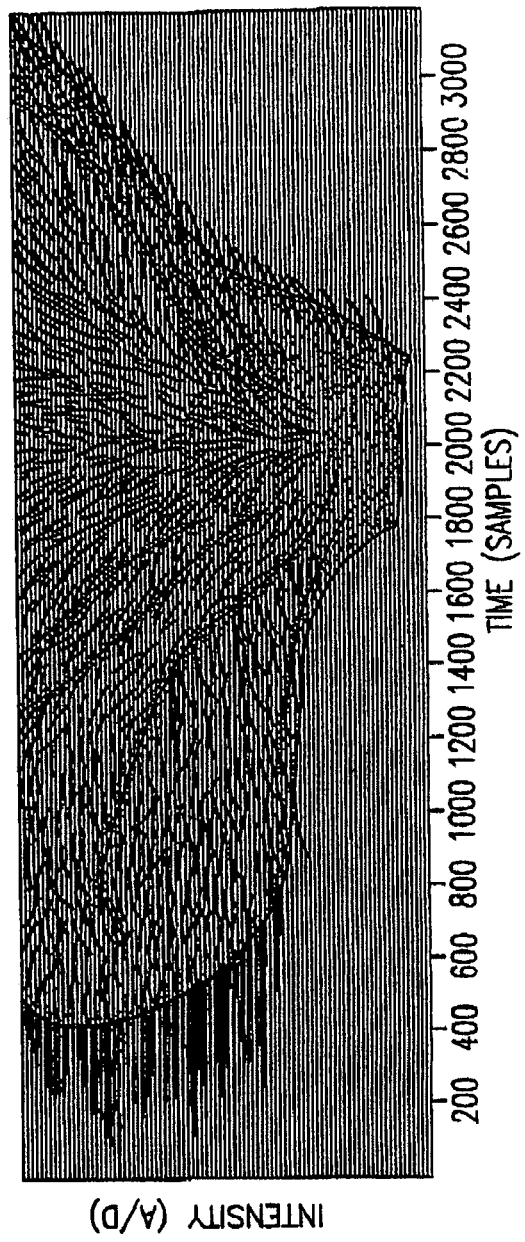

FIG. 18 shows a high density compilation of the HF signals acquired from the tracks across the gnat wing.

Figure 19:
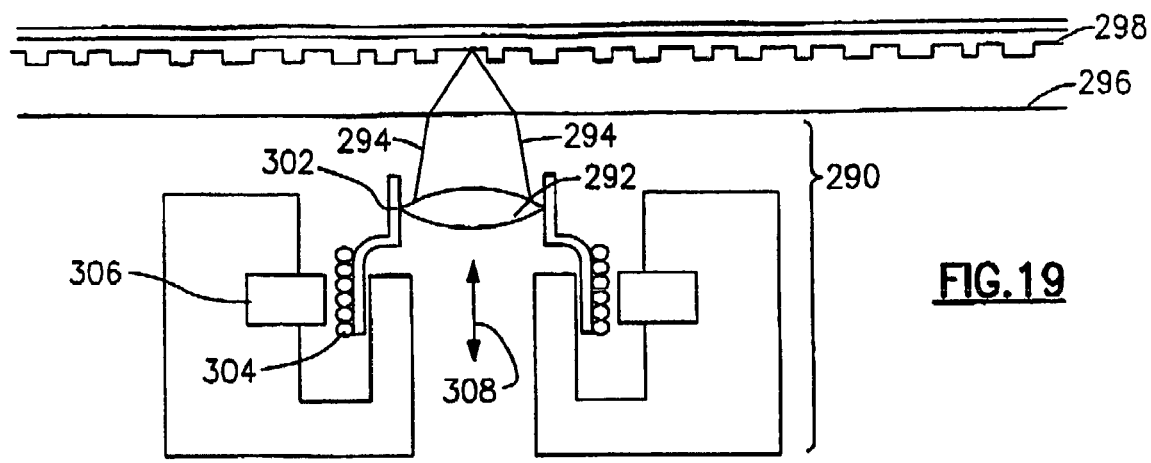

FIG. 19 shows an objective lens focusing mechanism.

Figure 20:
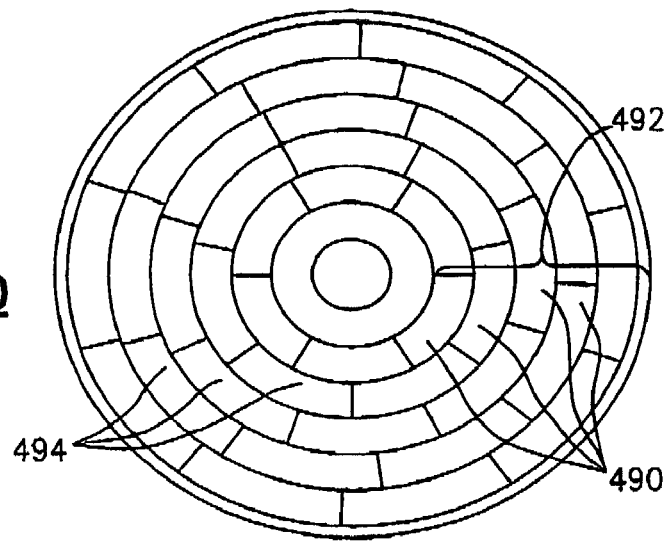

FIG. 20 illustrates the data and surface organization of a zoned constant linear velocity (ZCLV) format.

Figure 21:
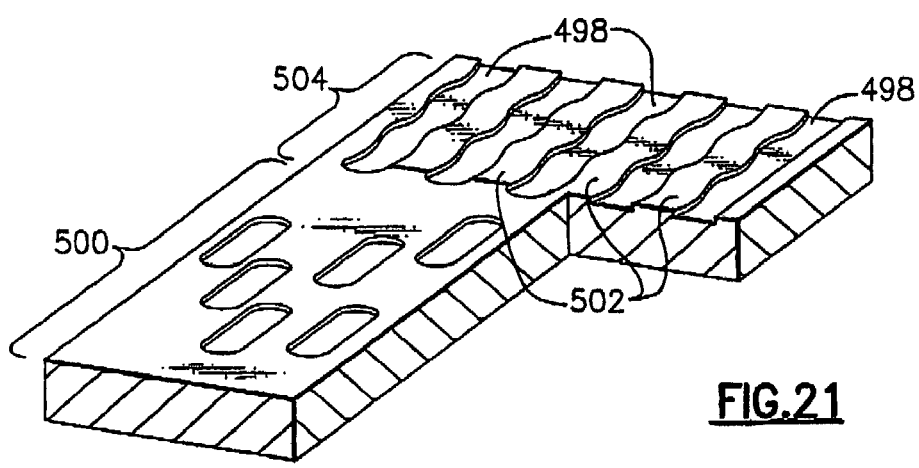

FIG. 21 is an enlarged perspective view of a portion of a section of a ZCLV disc, wherein the portion has a pre-groove area followed by a wobble groove area.

Figure 22:
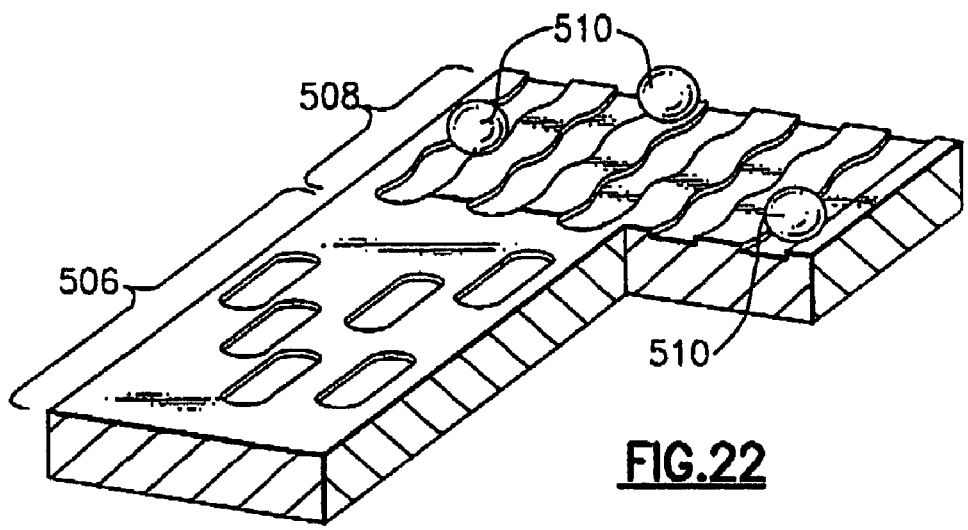

FIG. 22 depicts investigational features placed in the wobble area of one section in a ZCLV disc.

Figure 23:
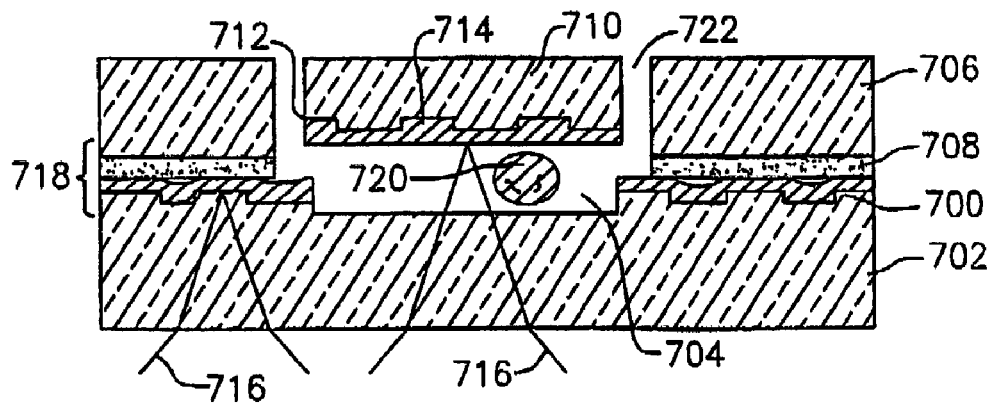

FIG. 23 demonstrates a dual data layer disc that includes a cut-away area or window, a sample chamber and channels.

Figure 24:
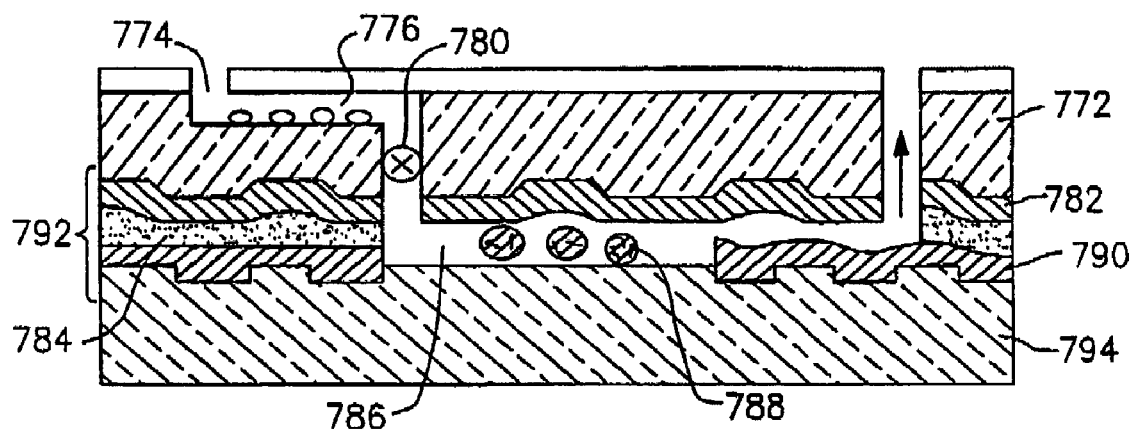

FIG. 24 shows a dual data layer disc assembly including channels and a sample chamber.

Figure 25:
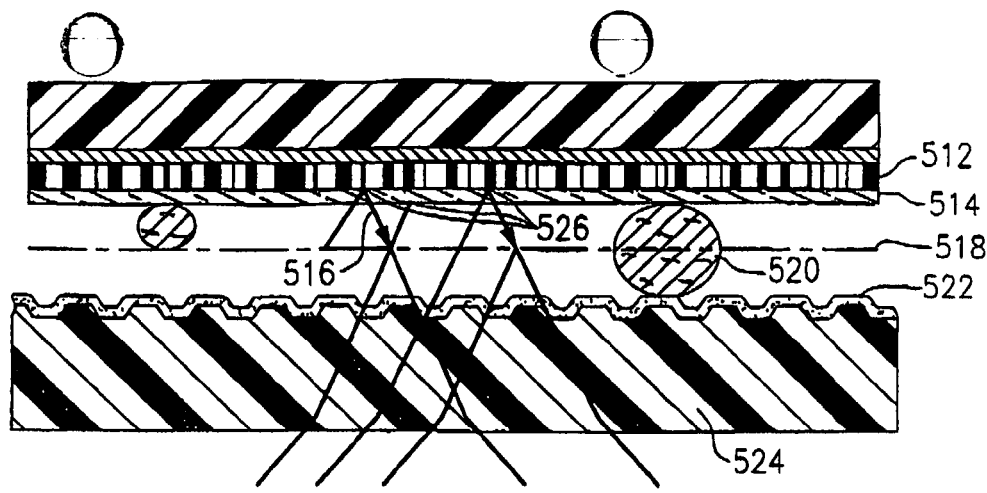

FIG. 25 illustrates a dual data layer optical disc assembly including a reflective hologram as the laser-distal data layer.

Figure 26:
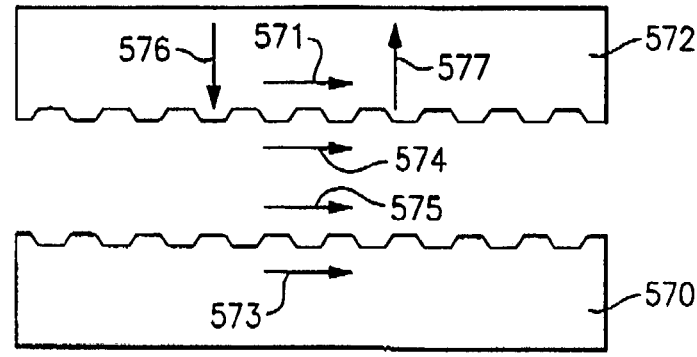

FIG. 26 schematically illustrates possible spatial relationships between the analyte section and the operational surfaces of a dual data layer optical disc.

Figure 27:
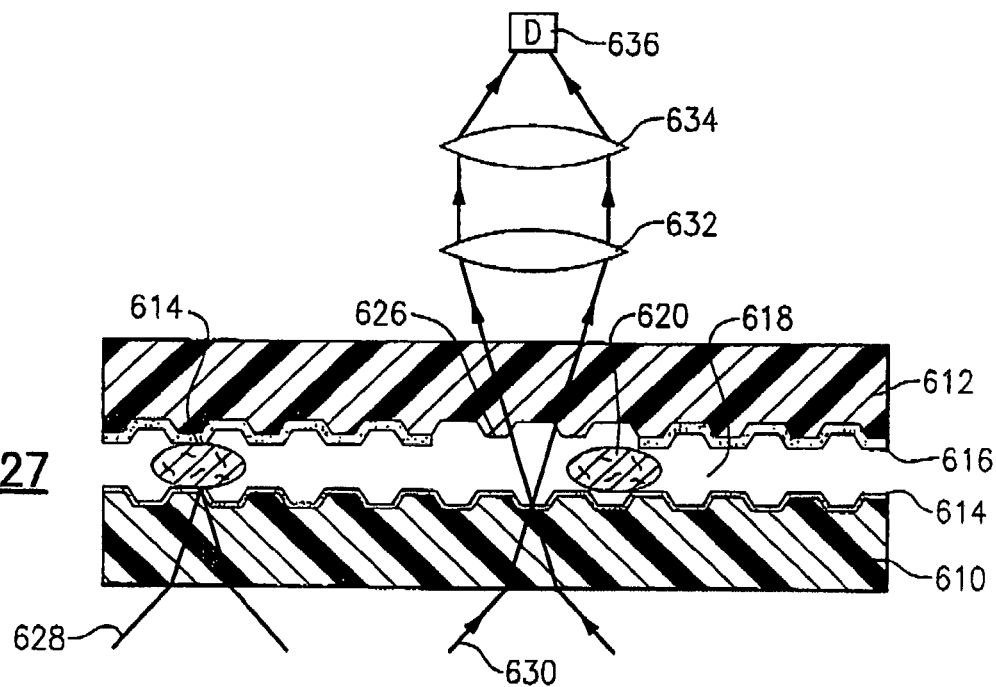

FIG. 27 demonstrates a dual data layer optical disc including a cut-away area or window in the laser-distal operational surface.

DESCRIPTION OF EMBODIMENTS OF THE INVENTION

This invention relates to an optical disc assembly which preferably includes at least two data layers and which is configured to receive an analyte of interest that can be detected by an optical disc reader. Each data layer may have encoded operational information. The analyte may be a physical specimen, such as a biological, chemical, or biochemical specimen, or a product produced by a biological, chemical, or biochemical reaction that is carried out in the optical disc assembly. The optical disc reader preferably is a DVD reader or a modification thereof. The optical disc reader preferably can read at least two data layers. The optical disc reader may be a standard optical disc reader or an optical disc reader modified therefrom. In certain cases, CD readers may be used to read the optical disc assembly of the present invention. For instance, a CD reader may be used when one data layer is sufficient for both the operation of the disc reader and the detection of the analyte. The optical disc assembly may be designed so that the association of the analyte with the disc assembly does not prevent the optical disc reader from tracking the disc assembly or performing other operational functions.

As used herein, various surfaces in an optical disc assembly can be numbered or named according to the order in which the light beam of the optical disc reader strikes or passes through them upon first occurrence. For example, when a compact disc (CD) is read by a CD reader, the laser beam of the CD reader first enters the disc through a surface of a polycarbonate layer. The polycarbonate layer also is known as the polycarbonate disc or the substrate. This surface is referred to as the first surface or the laser-proximal surface of the polycarbonate layer. The laser beam proceeds through the polycarbonate layer and comes out through another surface of the polycarbonate layer. This latter surface is referred to as the second or the laser-distal surface of the polycarbonate layer. The laser beam proceeds to a reflective layer that is usually made of gold or other reflective material. The reflective layer is laser-distal to the polycarbonate layer. The laser beam is reflected back from the reflective layer, passing through the polycarbonate layer and returning to a detector of the CD reader.

When a CD-R disc is read by a CD-R reader, the laser beam of the reader enters the CD-R disc through the first surface of a polycarbonate layer. The laser beam proceeds through the polycarbonate layer and enters into a dye layer that is laid on the tracks embossed or impressed in the laser-distal surface of the polycarbonate layer. The polycarbonate layer is laser-proximal to the dye layer. The back surface of a CD-R disc, upon which labels or markings are laid, is referred to as the back plane. The back plane is the most laser-distal surface in the CD-R disc.

As used herein, "operational structures" or "operational features" in an optical disc assembly refer to optically readable structures which are impressed or encoded in the optical disc assembly and which enable an optical disc reader to track, synchronize, or perform other customized operational functions. Operational structures may act as phase components or provide interference patterns. Operational structures may have encoded speed information that enables the optical disc reader to rotate the disc assembly at a speed determinable from the speed information. Light returned from or passed over operational structures can be acquired by the optical disc reader to generate operational signals. These operational signals are used by the optical disc reader to track, focus, synchronize, or perform other operational functions.

Operational structures may be imprinted or impressed in a surface of a layer in the disc assembly. Such a layer is referred to as an "operational layer," and such a surface is referred to as an "operational surface." In a typical CD, the operational layer is the polycarbonate disc, and the operational surface is the laser-distal surface of the polycarbonate disc. A typical dual data layer DVD includes two operational layers: a laser-proximal operational layer ("layer 0") and a laser-distal operational layer ("layer 1"). The laser-proximal operational layer is located laser-proximal to the laser-distal operational layer. The laser-proximal operational layer includes an operational surface at its laser-distal surface. The laser-distal operational layer includes an operational surface at its laser-proximal surface. An optical disc may have more than two operational layers or operational surfaces. Preferred operational structures include, but are not limited to, wobble grooves, pits and lands, dye marks, or any combination thereof.

According to one aspect of the present invention, operational structures may be encoded in a hologram. Light returned from or transmitted through the hologram can create an image plane within which the encoded operational structures appear to be positioned. The encoded operational structures, as appearing in the image plane of the hologram, preferably are in the form of wobble grooves, tracks of pits and lands, or any other type of operational structures that may be physically impressed in an optical disc's operational layer.

Operational structures, impressed or encoded, may be in a variety of formats. Suitable formats for this invention include, but are not limited to, CD formats, DVD formats, any combination thereof, or other optical disc formats. CD formats include, but are not limited to, CD-ROM, CD-R, and CD-RW formats. DVD formats include, but are not limited to, DVD-R, DVD-RW, and DVD-RAM formats. As appreciated by those of skill in the art, other CD or DVD formats or other optical disc formats, including those that have been or will be developed in the future, may be used in the present invention.

"Investigational structures" or "investigational features" refers to the structures, features, or samples (including any aspects, attributes, or characteristics thereof) that are placed in an optical disc assembly to be examined. An investigational structure or feature may be an analyte which includes a physical specimen, such as a biological, chemical, or biochemical sample, or a product produced by a biological, chemical, or biochemical reaction conducted in the optical disc assembly. An investigational structure or feature may also be part of an analyte. Investigational structures or features usually cannot provide operational information. Investigational structures or features typically are not imprinted or impressed in the optical disc assembly. They usually are not encoded in a hologram. Preferably, investigational structures or features are replaceably disposed in the optical disc assembly. Investigational structures or features may be chemical, biochemical, or biological in nature. They may also be signal or reporter elements such as beads.

Association of investigational structures with an optical disc assembly of the present invention does not prevent the optical disc reader from operating the optical disc assembly. In order to operate an optical disc assembly, the optical disc reader usually needs to (1) accurately focus above the operational surface of the disc assembly, (2) accurately track the operational surface or use some form of radial movement across the disc surface, (3) maintain a form of speed control, (4) maintain proper power control by logical information gathered from the disc assembly, and (5) respond to logic information that may be used to control, for example, the position of the objective assembly, the speed of rotation, or the focusing position of the laser beam.

An analyte that is disposed in the optical disc assembly of the present invention can be read or detected by an optical disc reader. As used herein, an analyte can be read or detected by an optical disc reader if the optical disc reader can generate a signal indicative of at least the presence of the analyte. The present invention also contemplates the use of an optical disc reader to generate signals indicative of other properties of the analyte, such as the concentration or dimension of the analyte.

The multiple data layer optical disc of this invention allows the analyte to be located within various planes in the optical disc. Focus control information or logic switches can be encoded in the optical disc. These focus control information or logic switches may direct the optical disc reader to move the focal point of the reader's reading beam for instance, from one data layer to another data layer, or from one operational surface to the analyte, or from one assay area to another assay area.

In accordance with one aspect of the present invention, the optical disc assembly includes at least a first data layer, a second data layer, and an analyte section. At least one of the two data layers is an operational layer. The operational layer contains an operational surface in which operational structures are impressed or otherwise encoded. The operational structures have encoded operational information that enables the optical disc reader to operate the disc assembly. In particular, the operational structures may have encoded tracking information that allows the disc reader to track the operational structures. The operational structures may also have encoded speed information enabling the disc reader to rotate the disc assembly at a speed determinable from the encoded speed information. Preferably, the operational structures are coated with a reflective layer including a reflective material, such as metal, aluminum, gold, silver, or silicon. As used herein, a reflective layer can be semi-reflective and semi-transmissive. Light reflected from the reflective layer can be acquired by the disc reader to generate operational signals for focusing, tracking, or performing other operational functions. The operational layer may be a hologram in which the operational structures are encoded. In a preferred embodiment, both the first data layer and the second data layer are operational layers.

Speed information encoded in the operational structures allows an optical disc reader to rotate the optical disc assembly at a determinable speed. Speed information may be encoded in frame synchronization words that allow the optical disc reader to adjust the disc speed to keep a desired data rate. The speed information may also be encoded in a wobble groove. The wobble groove can produce signals useful for regulating the disc speed. In addition, special marks or logic information can be used to provide speed information. In one embodiment, the optical disc reader rotates the optical disc assembly with a constant linear velocity.

At least one of the two data layers includes a logic switch or has encoded focus control information. The logic switch or the focus control information controls the movement of the reading beam's focus, and may allow the disc reader to move the reading beam from one data layer to another data layer.

The analyte section is configured to receive at least an analyte of interest. The analyte section may be embedded in the disc assembly. It may be positioned between two layers of the disc assembly. It may also be located within a layer in the optical disc assembly. As used herein, a layer in a disc assembly refers to a thickness of material. For instance, a layer may be a substrate disc or a coating of reflective material. A layer may also be an insert that can be assembled into another layer in the disc assembly. A layer may be flat or not flat. A layer may be homogeneous or non-homogenous. The depth of a layer may be uniform or not uniform. A layer may be an assembly of several parts.

The analyte section may be the most laser-distal or the most laser proximal structure in the disc assembly. The analyte section may include channels, microfluidic channels, chambers, cavities, or other structures that are designed for the manipulation, creation, or retention of the analyte or investigational structure and features of interest. The analyte section may also be referred to as the component layer. An optical disc assembly may have more than one analyte section. The analyte section and the operational layer can be intermixed so long as the optical disc reader can retain control of focusing, tracking, velocity, and other operational functions. Analytes or investigational structures can be in the nanometer, micrometer, or millimeter range, and can be disposed, modified, or created in the analyte section.

Preferably, the optical disc assembly includes a lens layer. The lens layer may be used to focus the laser beam, for instance, on either the operational structures or the analyte. In one embodiment, the operational layer may function as a lens layer. In such a case, the operational structures may be embossed in the laser-distal surface of the operational layer. The refractive index of the lens layer can be selected to perform the desired focusing function. The lens layer typically is laser-proximal to the operational or investigational structures. Preferably, the lens layer includes a material selected from the group consisting of plastic and glass. More preferably, the lens layer consists of plastic, such as polycarbonate or polystyrene. In a highly preferred embodiment, the lens layer consists of polycarbonate. Other examples of material suitable for constructing a lens layer include polymethylacrylic, polyethylene, polypropylene, polyacrylate, polymethyl-methacrylate, polyvinylchloride, polytetrafluoroethylene, polyacetal, polysulfone, celluloseacetate, cellulosenitrate, nitrocellulose, or any mixtures or combinations thereof.

The optical disc assembly of the present invention preferably approximates the dimensions of a unitary disc. For instance, the disc assembly may have a radial diameter of between about 50 and 150 mm, preferably between about 75 and 130 mm, including 85 mm, 110 mm, and 120 mm. Preferably, the disc assembly has a depth or thickness with the range from about 0.8 to 2.4 mm, including the range from about 1.0 to 1.4 mm. More preferably, the disc assembly has a depth or thickness of between about 1.1 and 1.3 mm, including 1.2 mm. In one embodiment, the disc assembly may have a thickness of about 0.6 mm. The disc assembly may be flat or not flat, circular or non-circular. The disc assembly may have a central hole through which the disc assembly can be coupled to a disc reader.

Figure 1:
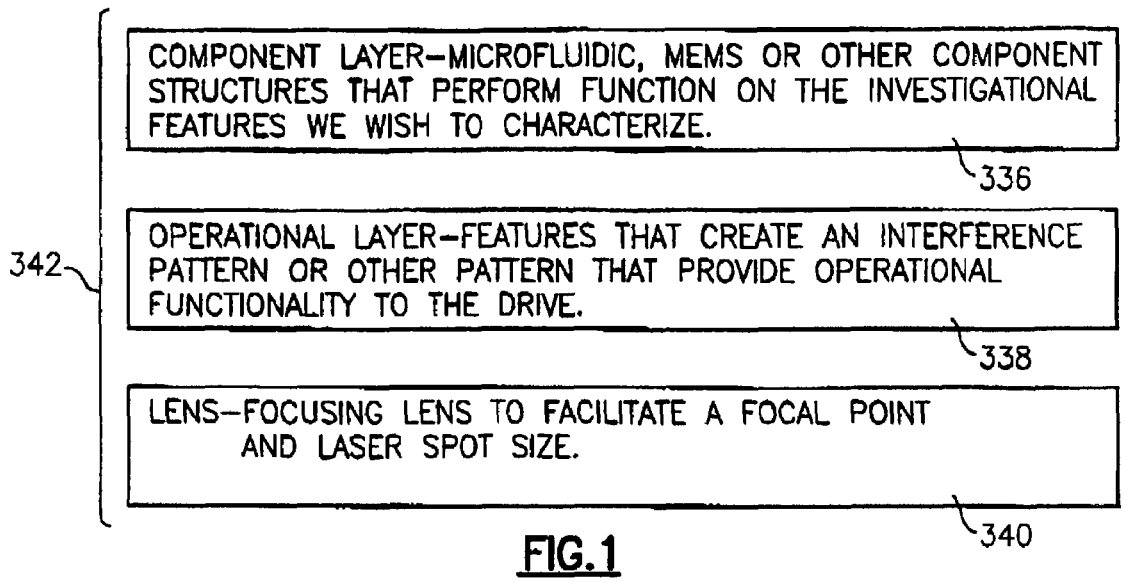

With reference now to FIG. 1, there is shown a diagram illustrating the functional layers in an optical disc according to one embodiment of this invention. The optical disc assembly has at least an operational layer 338, a component layer 336, and a lens layer 340. The optical disc assembly further includes another data layer that may have encoded operational information or other information, such as information relating to conducting an assay on the analyte. The disc assembly encompasses the focusing range of the reading beam. The operational layer 338 contains the operational structures that can be used by the disc reader to track the disc assembly. The operational structures may create an interference pattern or other patterns that provide operational functionality to the disc reader. The component layer 336 contains the investigational structures as well as other structures that are related to the manipulation, creation, or retention of the investigational structures. The component layer may include microfluidic channels. The lens layer 340 may focus the laser beam either on the operational structures or on the investigational structures. The component layer, the operational layer and the lens layer may be intermixed or overlapped so long as the disc reader can retain control of the focusing, tracking, and speed. The measurement area 342 represents the area which are readable by the disc reader's laser. The laser's focal point can roam across the measurement area. The measurement area may encompass any of the component layer, the operational layer, the lens layer, or a portion thereof.

Figure 2:
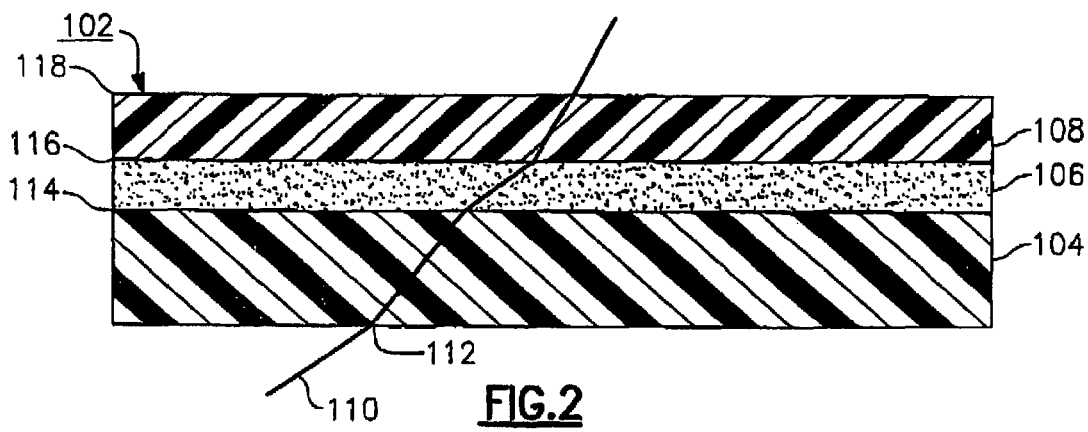
FIG. 2 shows a cross-sectional view of an optical stack including three layers of refractive material.

Different layers in an optical disc assembly may have different optical properties and can impose different optical effects on the light beam that passes through these layers. These optical effects include, for example, reflection, refraction, transmission, or absorption. FIG. 2 is a simplified example showing the effects of different layers on the passage of a light beam.

The optical disc 102 in FIG. 2 includes three layers of refractive material, 104, 106, and 108. The refractive properties of these layers may differ based on their compositions. The different refractive properties create changes in the light beam 110 as the light beam passes through these layers. The layers may be named in order of their first contact with the light beam 110. The light beam 110 enters through the bottom surface 112 and exits at the top surface 118. Therefore, layer 104 may be referred to as the most laser-proximal layer, and layer 108 as the most laser-distal layer. Layer 106 is laser-distal to layer 104, and laser-proximal to layer 108.

The light beam 110 enters layer 104 at surface 112. The light beam is bent and slowed because of the refractive property of layer 104. The light beam exits layer 104 at surface 114, and then enters layer 106 which has a different refractive property, therefore further altering the angle and speed of the light beam. As the light beam exits layer 106, it enters layer 108 at surface 116 with a further changed angle and speed. The light beam exits layer 108 at surface 118. Surface 112 is laser-proximal to surface 114 which is laser-proximal to surface 116. Surface 118 is the most laser-distal surface in the optical stack 102.

Figure 3:
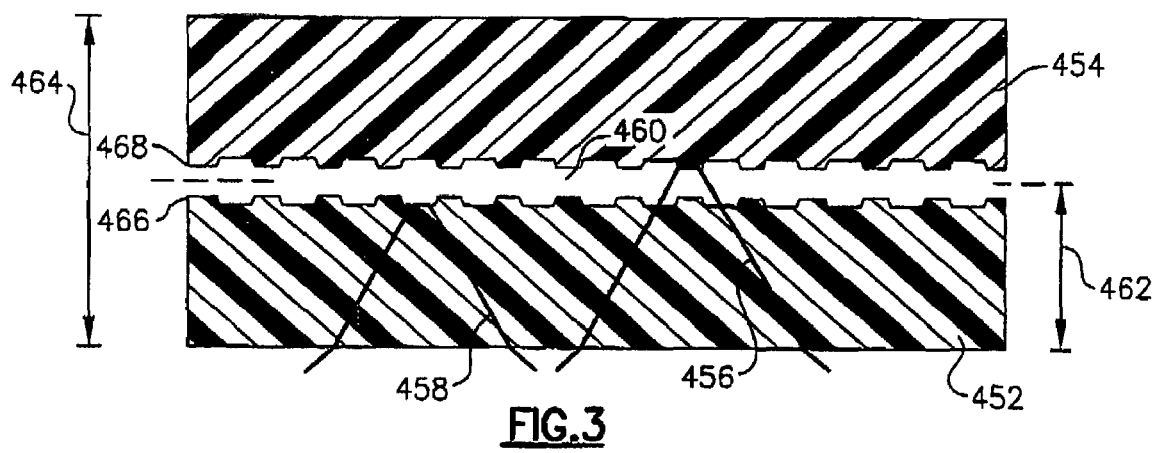
FIG. 3 is a cross-section view of a dual data layer optical disc, within which the laser's focal point is capable of moving between the operational surfaces.

In one embodiment, the optical disc assembly of this invention is designed based on a modification of an industry standard design, such as a standard DVD that includes, but is not limited to, a standard DVD-RAM, DVD-R, or DVD-RW disc. FIG. 3 schematically illustrates a DVD-type disc that may be used in the present invention. The DVD-type disc includes two operational layers. The laser-proximal operational layer 452 serves as a lens layer and may focus the laser beam 458 on its laser-distal surface 466. The layer 452 may also focus the laser beam 456 on the laser-proximal surface 468 of the laser-distal operational layer 454. The movement of the laser beam's focus from the surface 466 to the surface 468 may be regulated by a logic switch encoded in the DVD disc. The thickness 462 of the layer 452 and the thickness 464 of the disc assembly can be varied so that a desirable focusing and disc stability are achieved. Preferably, the thickness 462 is about 0.6 mm, and the thickness 464 is about 1.2 mm. The thickness of the layer 452 may be selected to optimize the optical properties of the layer 452 in order to facilitate the detection of the investigational structures.

Both the surface 466 and the surface 468 may be impressed with operational structures. These operational structures may include wobble grooves, pits and lands, or other suitable optically readable structures or features that may provide operational information. The operational structures may be in a CD format, a DVD format, or a combination thereof. The operational structures may be organized in a ZCLV format. The operational structures impressed in the surface 466 may be in a format different from the operational structures impressed in the surface 468. For instance, the operational structures in one layer may be in a CD format, whereas the operational structures in the other layer is in a DVD format.

The operational structures impressed in the surface 466 may be coated with a semi-reflective layer that is partly reflective and partly transmissive. This semi-reflective layer is usually a thin layer of reflective or semi-reflective material, such as silicon, tellurium, selenium, bismuth, aluminum, silver, copper, or other suitable metals or alloys. The thickness of the semi-reflective layer may range from 10 nm to 100 nm. The reflectivity of the semi-reflective layer may preferably range from about 18 to 30%. The operational structures impressed in the surface 468 may be coated with another reflective layer. The reflectivity of this second reflective layer may be selected in order to obviate readjustment of gain control when the disc reader switches its reading between the layer 452 and the layer 454. In one case, the reflectivity of this second reflective layer may be about 70%.

The space area 460 between the layers 452 and 454 may be about 40 to 70 micrometers wide. It may contain adhesive materials to bind the layers 452 and 454 together. The optical properties of material or materials filled in the space area may be selected to optimize the reflectivity of the surfaces 466 and 468.

The analyte section may be located with the space area 460. The analyte section may also be embedded, partially or totally, in either of the layers 452 and 454. The analyte can be disposed at least on five different planes in the DVD disc: the analyte can be positioned laser-proximal to the surface 466, on the surface 466, within the space area 460, on the surface 468, or laser-distal to the surface 468. In one embodiment, the analyte is positioned on one of the operational surfaces, and the laser beam is focused on and scans over the operational surface to detect the analyte. In another embodiment, the analyte is physically segregated from the operational surfaces 466 and 468. The laser beam may be focused on one of the operational surfaces 466 and 468, and the analyte becomes detectable when it is properly positioned in the optical path of the laser beam. The segregation of the analyte from the operational surfaces may facilitate concurrent and discriminable acquisition of both operational signals and investigational signals that are indicative of the presence of the analyte.

Logical information can be encoded in the disc, preferably in the inner diameter of one of the surfaces 466 and 468. As the logical information is read by the disc reader, a logical switch may be activated so that the focal point of the reading beam can be moved from one operational surface to the other. Assay information may also be encoded in the disc for conducting an assay on the analyte.

In one embodiment, the optical properties of the layer 452 or the surface 466 may be designed so as to facilitate the reading of information encoded in the surface 468. For instance, certain structures or surfaces in the layer 452 or in the surface 466 may have a modified refractive or reflective property.

In another embodiment, the optical disc reader uses a solid immersion lens to facilitate detection of biological, chemical, or biochemical samples disposed in the disc.

In a preferred embodiment, the operational structures impressed in either of the surfaces 466 and 468 include a spiral wobble groove. The spiral wobble groove may run from the inner diameter of the disc to the outer diameter of the disc, or in the opposite direction. Preferably, both the surfaces 466 and 468 include spiral wobble grooves. In one case, the spiral wobble groove impressed in one surface may run parallel to the spiral wobble groove impressed in the other surface. Consequently, the optical disc can switch between the operational layers while maintaining the reading direction by the optical disc reader. Alternatively, the spiral wobble groove in one surface may run in the opposite direction as compared to the spiral wobble groove impressed in the other surface. As used herein, a spiral wobble groove can be considered as a series of wobble grooves connected consecutively to form a spiral track.

Figure 4:
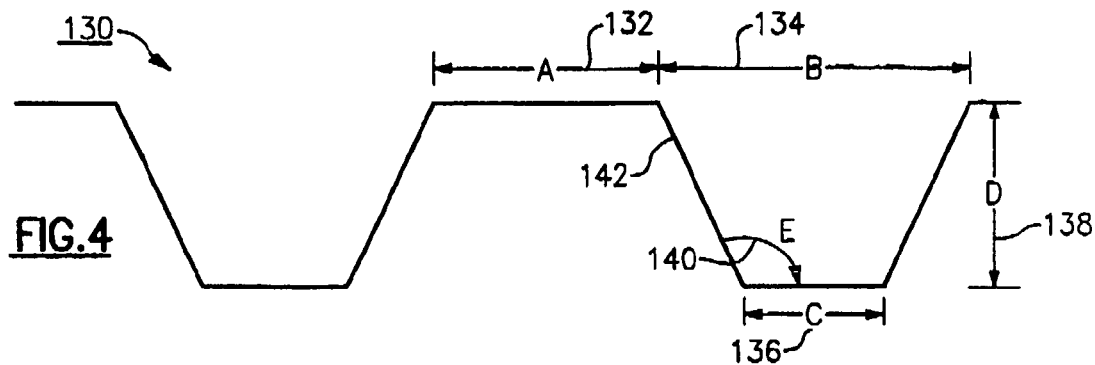
FIG. 4 is a diagram showing the geometry of a wobbled groove as it is embossed in an operational surface.

Wobble groove is a preferred operational structure used in the present invention. FIG. 4 demonstrates the geometry of wobble grooves. As with other figures used herein, FIG. 4 is not drawn to scale. FIG. 4 shows two adjacent wobbled grooves. Measurement A, 132, represents the distance between two adjacent wobble grooves in a spiral track. Measurement B, 134, denotes the width of the top of the wobble groove. Measurement C, 136, represents the width of the bottom of the wobble groove. Measurement D, 138, shows the depth of the groove. In a standard DVD disc, the wobble groove depth can be 50 nanometers. As used in the present invention, the depth of the wobble groove preferably is approximately ⅛ of the effective wavelength of the laser light in the layer that is located immediately laser-proximal to the operational surface. Such a depth may provide a strong tracking signal. The wobble groove may also have a depth approximately equal to any odd multiple of ⅛th of the effective wavelength, such as ⅜ths or ⅝ths. The depth of the groove may remain substantially constant along the wobble groove. The angle E, 140, between the side-wall 142 and the bottom of the wobble groove has an important effect on light that encounters the wobbled groove.

Figure 5:
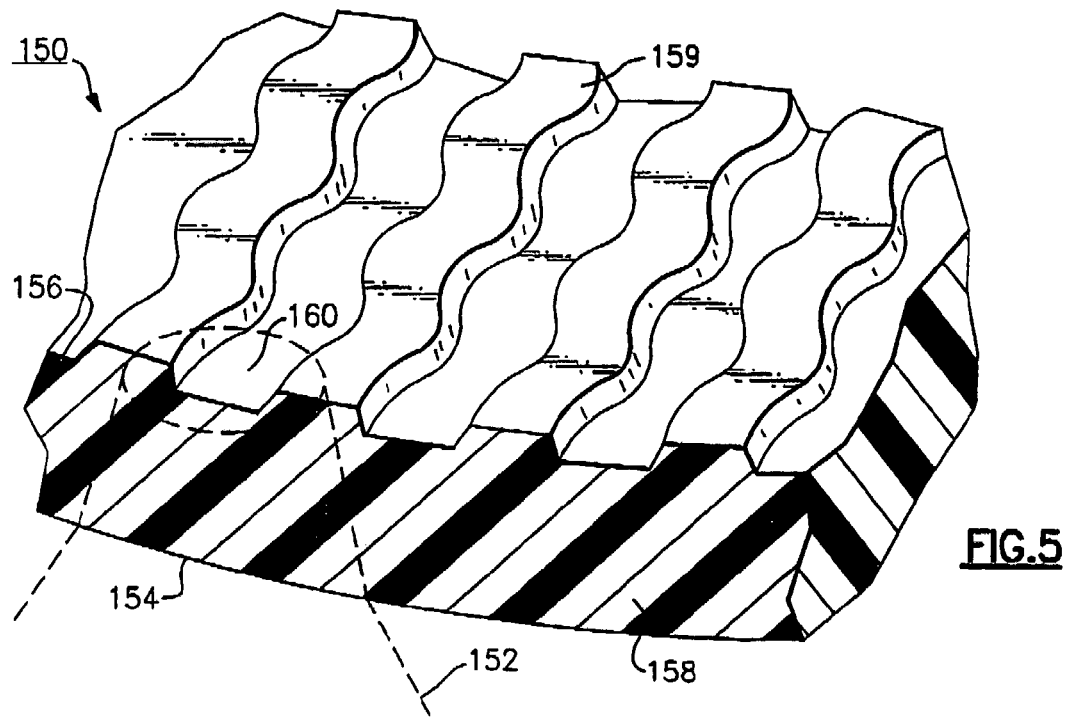
FIG. 5 shows wobbled grooves impressed in an operational surface, wherein the operational surface is at the laser-distal surface of the operational layer.

FIG. 5 illustrates an interaction of a wobble groove with a reading laser beam. Laser beam 152 enters the operational layer 158 at its laser-proximal surface 154. The light is bent according to the refractive property of the layer 158. The focus of the laser beam 152 encompasses the bottom of wobble groove 160. Wobble groove 160 is embossed in the laser-distal surface 156 of layer 158. Reference numeral 159 denotes a land of the wobble groove.

Preferably, no dye is laid down in the wobble groove, or the dye is laid down in discrete patterns so as to facilitate drive control during the examination of investigational structures or features. The groove preferably is coated with a layer of reflective or semi-reflective material. The reflective or semi-reflective layer preferably is positioned sufficiently close to the groove structure so as to provide adequate reflection when the laser light focuses on the groove structure. In addition, the pitch and angle of the groove walls can be selected to facilitate the detection of investigational features that are placed in the disc.

Figure 6:
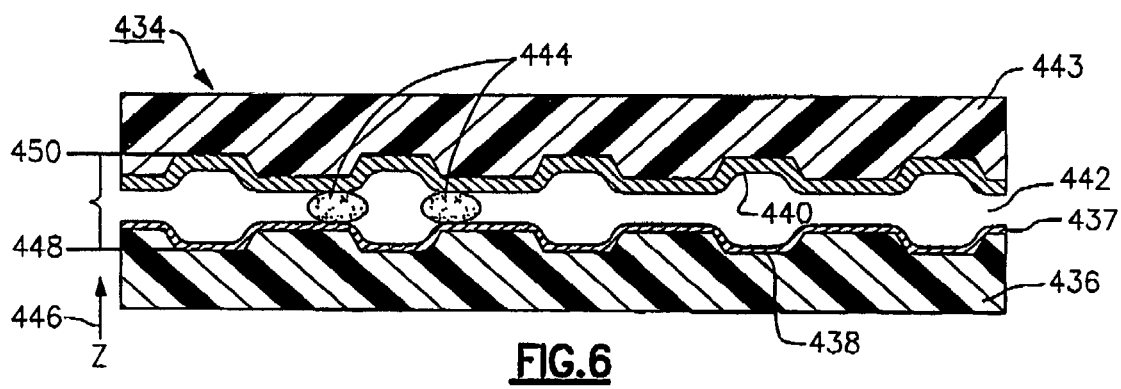
FIG. 6 depicts a cross-section view of a dual data layer optical disc assembly which includes a laser-proximal operational layer having operational structures coated with a partly reflective and partly transmissive layer, a laser-distal operational layer having operational structures coated with a reflective layer, and a analyte section configured to receive analytes.

In one embodiment, the analyte section is located within the space area between two operational layers. FIG. 6 shows a dual operational layer optical disc 434 that includes analytes in the space area. The laser-proximal operational layer 436 serves as a lens layer that includes a transparent optical material, such as polycarbonate. The transparent optical material has an index of refraction chosen to assist the focusing of the laser beam. The operational structures 438, including wobble grooves, are impressed at the laser-distal surface of the operational layer 436, and are coated with a thin, semi-reflective and semi-transmissive layer 437. The reading laser beam can pass through the semi-reflective layer 437 to reach a second reflective layer 440. The reflective layer 440 coats the operational structures impressed in the laser-proximal surface of the laser-distal operational layer 443. The analyte section, which contains analytes 444, is located within the space area 442. The space area 442 may have a thickness of about 40 to 70 microns, and may contain an adhesive material to bind the layer 436 to the layer 443. The adhesive material preferably has an index of refraction that is close to the index of refraction of the first operational layer 436.

Figure 7:
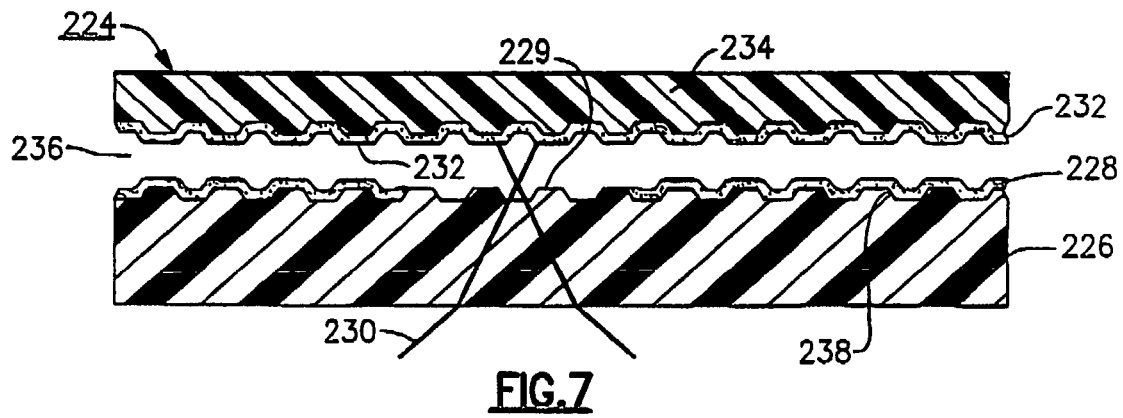
FIG. 7 shows a dual data layer optical disc that has a cut-away area or window in the operational surface.

FIG. 7 illustrates another dual operational layer optical disc 434 that includes a cut-away area or window in the operational surface of the operational layer 226. As used herein, a "cut-away" area refers to an area in the operational surface, wherein the area either lacks operational structures, or the operational structures in the area are changed in certain ways. The operational structures in a cut-away area or window may be deprived of reflective coatings, or be coated with a reflective material having a different reflectivity than the reflective material coated on other regions in the operational surface. In FIG. 7, the cut-away area or window 229 lacks reflective coatings. The laser beam 230 can pass through the cut-away area or window 229 to reach the reflective layer 232 which coats the operational surface of the operational layer 234. In one embodiment, a surface of the analyte section includes or is adjacent to the cut-away area or window. Analytes may be placed on the cut-away area or window. As appreciated by one of skill in the art, a cut-away area or window may also be created in the operational surface of the operational layer 234.

Analytes or investigational structures that are disposed in an optical disc assembly of the present invention can be read or detected using an optical disc reader, such as a CD reader or a DVD reader. As used herein, CD readers include, but are not limited to, CD-ROM readers, CD Recordable (CD-R) readers, CD-Rewriteable (CD-RW) readers, or any reader capable of reading CD-format discs. Industry standard CD readers may be used in the present invention. A preferred CD reader for this invention is a CD-RW reader or a modification thereof. As used herein, DVD readers include, but are not limited to, DVD-R readers, DVD-RAM readers, DVD-RW readers, or any reader that can read DVD-format discs. Industry standard DVD readers may be used. As would be appreciated by one of skill in the art, other CD readers, DVD readers or optical disc readers, including those that have been or will be developed in the future, may be used in the present invention.

Signals indicative of the presence or other properties of an investigational structure or feature can be generated by the optical disc reader. The disc reader directs a reading beam of electromagnetic radiation, typically a laser beam, to the optical disc assembly in which the investigational structure is disposed. The disc reader can scan the beam over the area in which the investigational structure is held. The scanning beam can be either reflected from or transmitted through the disc assembly. The reflected or transmitted radiation may be acquired by a detector in the disc reader. Radiation thus acquired can be used to produce signals indicative of the presence or other properties of the investigational structure. Different types of lasers with different wavelengths may be used in the present invention. Whereas a standard optical disc reader is used, the disc reader may be connected to circuitry for processing the signals indicative of the presence or other properties of the investigational structure.

Radiation acquired by the detector of the optical disc reader can also be used to generate operational signals, such as focusing servo signals, tracking servo signals, synchronization signals, power control signals, or logic signals. The focusing servo signals can be generated from at least three focusing techniques: critical angle focusing, knife edge focusing, and preferably, astigmatic focusing. Tracking servo signals can be generated from at least four types of tracking techniques: one beam-push-pull tracking, three beam outrigger tracking, differential phase detection tracking, and one beam high frequency wobble tracking. Synchronization signals may be generated from at least three different methods: bit clock synchronization or bit pattern synchronization, zoned clocking method, and wobbling groove synchronization. Other techniques may also be employed to generate focusing servo signals, tracking servo signals, or synchronization signals. Logic signals can be produced from various optical disc formats. Logic signals can be used to perform position sensing, power control, radial and tangential location, layer sensing, density detection, or other functions.

Figure 8:
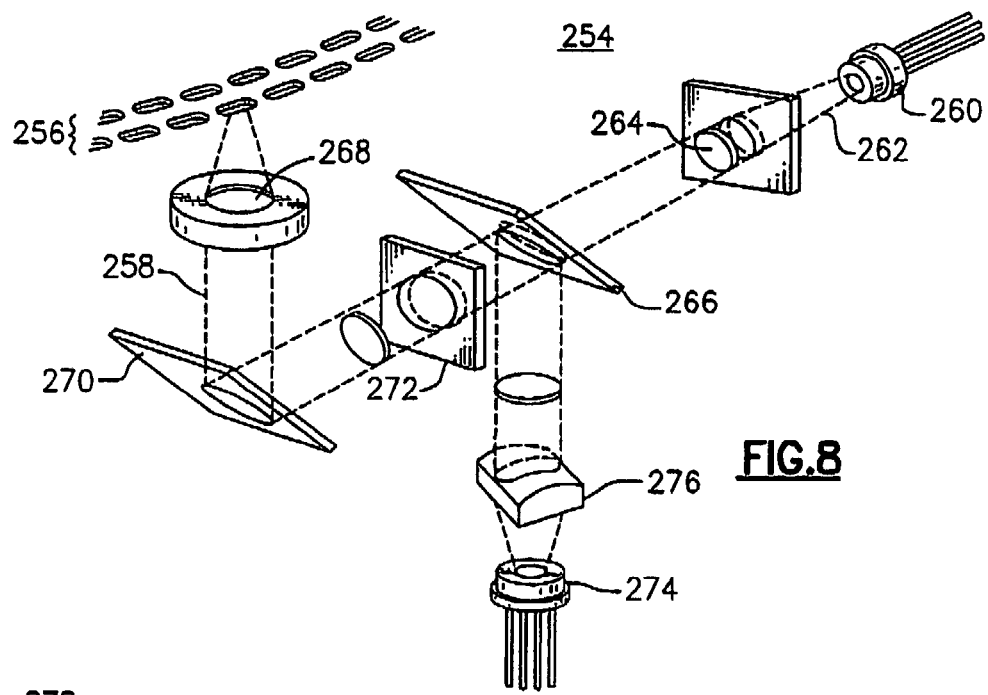
FIG. 8 illustrates an optical disc reader's optical pickup.

Preferably, the optical pickup as shown in FIG. 8 is used to both track the optical disc assembly and detect the investigational structure disposed therein. The optical pickup in FIG. 8, or similar optical pickups, may be used in both CD readers and DVD readers. The optical pickup 254 contains a laser source 260, which typically is a laser diode. The laser source emits a laser beam 262. The laser beam is collimated by a collimator lens 264. The collimated beam is then directed toward the optical disc through a polarization beam splitter 266. The objective lens 268 focuses the laser beam onto a small spot on the operational surface in the optical disc. The operational surface includes tracks of pits and lands 256. The surface preferably is coated with a reflective layer, so that the laser beam can be reflected therefrom and then directed by the objective lens 268, the mirror 270 and the quarter wave plate 272 to the beam splitter 266. As the light is now polarized in a different direction as compared to the source polarization, it can be directed by the beam splitter towards the photodiode detector 274. A cylindrical lens 276 may serve as an astigmatic element to introduce astigmatism in the reflected laser beam for the purpose of focusing.

Figure 9:
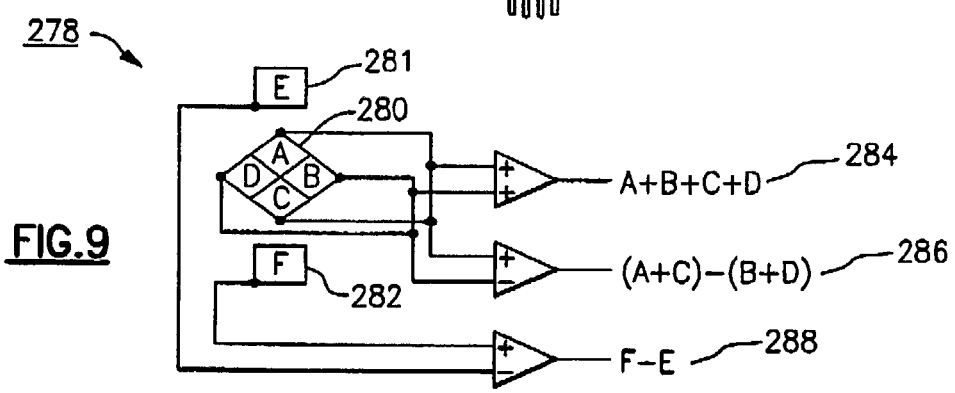
FIG. 9 is a schematic diagram of a quad detector.

In a preferred embodiment, the laser beam is split into three beams, consisting of a main beam and two tracking beams, and the detector is a quad detector. FIG. 9 shows a quad detector 278, which includes a central quad detector 280 flanked by two additional sensor elements E 281 and F 282. The main beam is centered on a track of operational structures. The tracking beams fall on either side of the track. By design, the three beams are reflected from the optical disc and then directed to the quad detector 278 such that the main beam falls on the central quad detector 280, which includes sensor elements A, B, C, and D, while the tracking beams fall on the sensor elements E 281 and F 282. The sum of the signals from the central quad detector, i.e. A+B+C+D, provides the radio frequency (RF) signal 284, also referred to as the high frequency (HF) or the quad-sum signal. A tracking error signal (TE signal) 288 may be obtained from the difference between E and F. Because astigmatism is introduced by the cylindrical lens astigmatic element, a focus error signal (FE signal) 286 may be obtained from the difference between A+C and B+D signals. Other combinations of the signals from A through F may be obtainable, as appreciated by one of ordinary skill in the art. These combinations of signals may be used to track the disc and read the investigational structure disposed in the disc. A quad detector and a similar optical design may be employed in both a CD reader or a DVD reader.

In one embodiment, the quad-sum signal is used for extracting information indicative of the presence or other properties of the investigational structure disposed in the disc assembly. Preferably, the disc assembly includes a wobble groove that is trackable by a disc reader. Suitable disc readers include, but are not limited to, CD-RW readers or preferably DVD readers. The use of the wobble groove enables the segregation of the tracking signal from the quad sum signal, permitting the quad sum signal to be used to detect signals from investigational structures. If the investigational structure is small enough, an electrical deflection may be detected in the quad-sum signal, while no such a deflection, or a comparatively smaller electrical impulse, will be noted in the tracking signal or the focusing servo signal.

The signals produced from a wobble groove can be used by the disc reader to maintain a constant linear scanning velocity at all points on the disc. This allows determination of the dimensional information of the investigational structure that is placed in the disc. Therefore, wobble grooves, or a combination of pits and wobble grooves, are the preferred operational structures employed in this invention.

Although the above-described embodiment uses the quad-sum signal and the wobble groove, signals other than the quad-sum signal and operational structures other than the wobble groove may be used for the detection of investigational structures. For instance, the focus error signal obtained by the critical angle method, as described in U.S. Pat. No. 5,629,514, may be used. The Foucault and astigmatism methods, as described in "The Compact Disc Handbook," by Pohlmann, A-R Editions, Inc. (1992), may also be employed. In addition, the tracking error signals obtained using the single beam push-pull method as described in "The Compact Disc Handbook," by Pohlmann, A-R Editions, Inc. (1992), the differential phase method as described in U.S. Pat. No. 5,130,963, or the single beam high frequency wobble method can be used for the present invention. The block error rate information, such as those used by a CD reader to reduce the effect of scratches on a CD surface, or the movement of the focusing servo may be used.

For more optical pickup designs and operational signals that may be used in the present invention, see "Compact Disc Technology," by Nakajima and Ogawa, IOS Press, Inc. (1992); "The Compact Disc Handbook," by Pohlmann, A-R Editions, Inc. (1992); "Digital Audio and Compact Disc Technology," by Baert et al. (eds.), Books Britain (1995); "CD-Rom Professional's CD-Recordable Handbook: The Complete Guide to Practical Desktop CD," Starrett et al. (eds.), ISBN: 0910965188 (1996). All these references are incorporated herein in their entirety by reference.

U.S. Provisional Application Ser. Nos. 60/270,095 and 60/292,108 further detail how to extract or process signals indicative of the presence of an investigational structure disposed in an optical disc assembly. Both applications are incorporated herein by reference.

Figure 10:
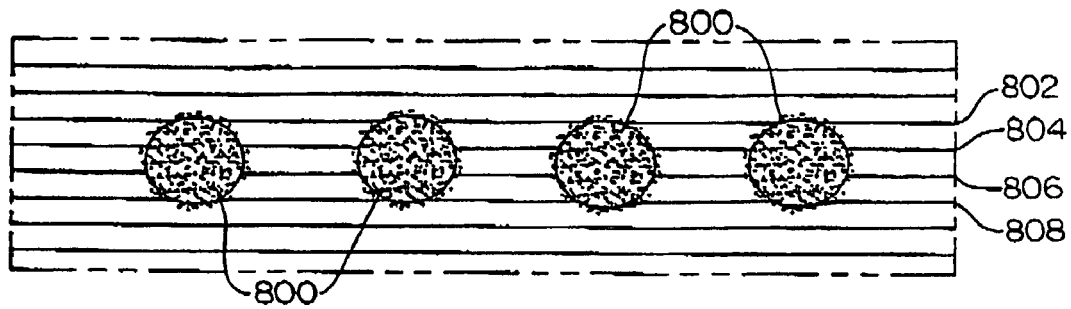
FIG. 10 depicts the positions of investigational structures relative to the tracks of operational structures.
Figure 11:
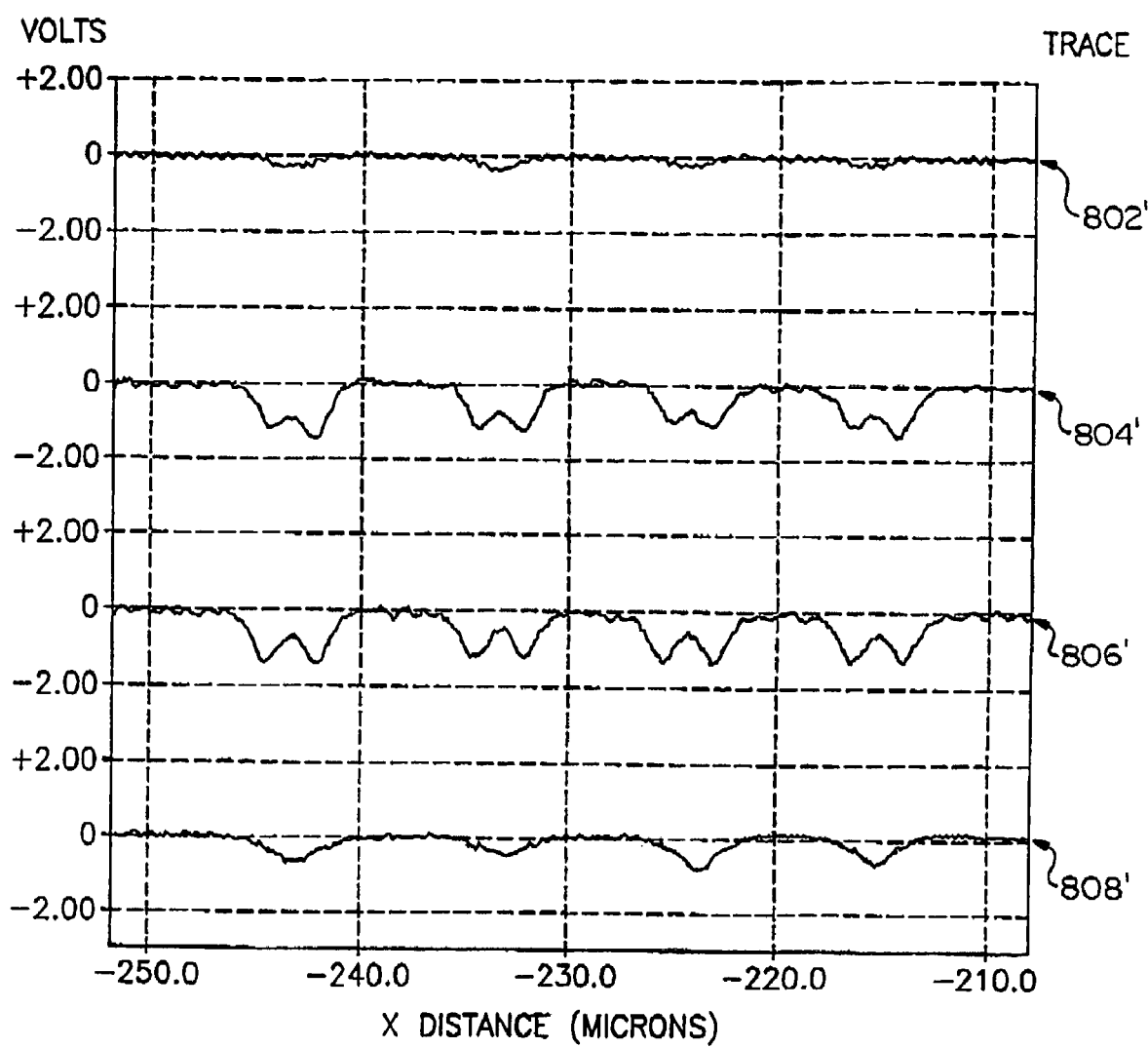
FIG. 11 shows the HF signals acquired from the tracks illustrated in FIG. 10.

FIGS. 10 and 11 illustrate a measurement of investigational structures using HF signals. In this case, the optical disc includes only one operational layer. However, the same detection principle can be easily applied to an optical disc that includes at least two operational layers. The analyte section in the optical disc used for FIGS. 10 and 11 is laser-proximal to the operational layer. In addition, the analyte section is positioned between the operational surface and a lens layer. FIG. 10 depicts the position of the investigational structures 800 relative to the tracks 802, 804, 806, and 808. The investigational structures 800 are held in the analyte section and positioned on the operational surface. The investigational structures 800 represented in FIG. 10 are 2.8 micrometers magnetic beads. Tracks 802, 804, 806, and 808 are embossed in the operational surface. Each track preferably is in the form of a wobble groove.

FIG. 11 shows the HF signals 802', 804', 806', and 808' that are acquired along the tracks 802, 804, 806, and 808, respectively. The HF signals shown in FIG. 11 have been digitalized and buffered. The HF signals 802', 804', 806', and 808' demonstrate the existence as well as the approximate dimension of the investigational structures 800.

Figure 12:
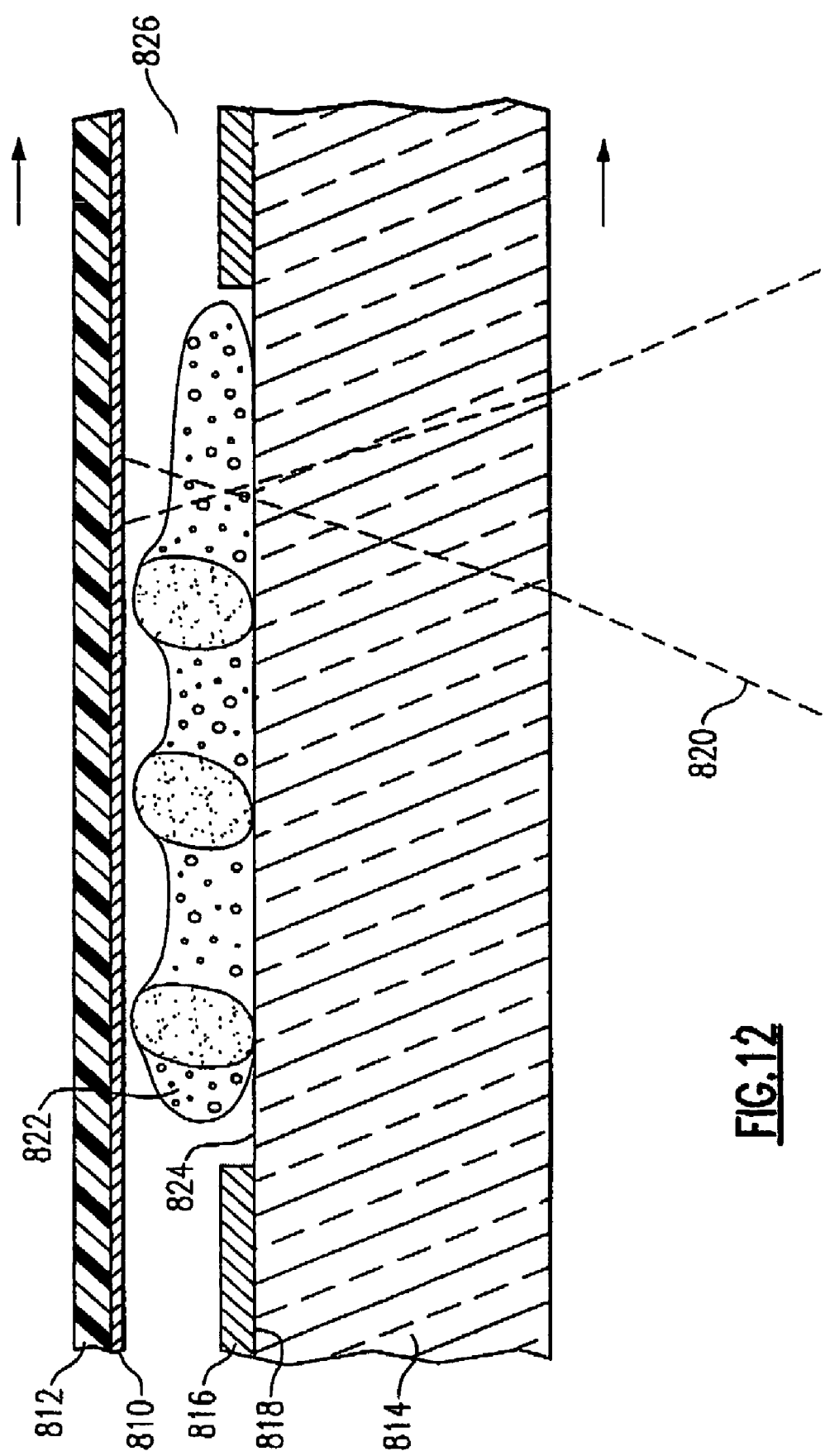
FIG. 12 shows an optical disc assembly including a gnat wing in a cut-away inspection channel.

FIGS. 12 through 18 illustrate the measurement of a gnat wing using HF signals. FIG. 18 is a cross-sectional view taken perpendicular to a radius of the optical disc assembly used in the measurement. In FIG. 12, the optical disc assembly includes an operational layer 814, a first reflective layer 816, a second reflective layer 810, and a cover 812. The analyte section 826 is located between the second reflective layer 810 and the operational layer 814. The operational surface 818 is the laser-distal surface of the operational layer 814. The operational surface 818 is embossed with tracks of operational structures, preferably, wobble grooves. The operational surface 818 is covered by the reflective layer 816. The operational surface has a cut-away area or window 824 that may lack the reflective coating 816. The gnat wing 822 is located in the analyte section 826 and positioned upon the cut-away area or window 824. The laser beam 820 can pass through the operational layer 814, the cut-away area or window 824 and the gnat wing 822, and then be reflected by the reflective layer 810.

Figure 13:
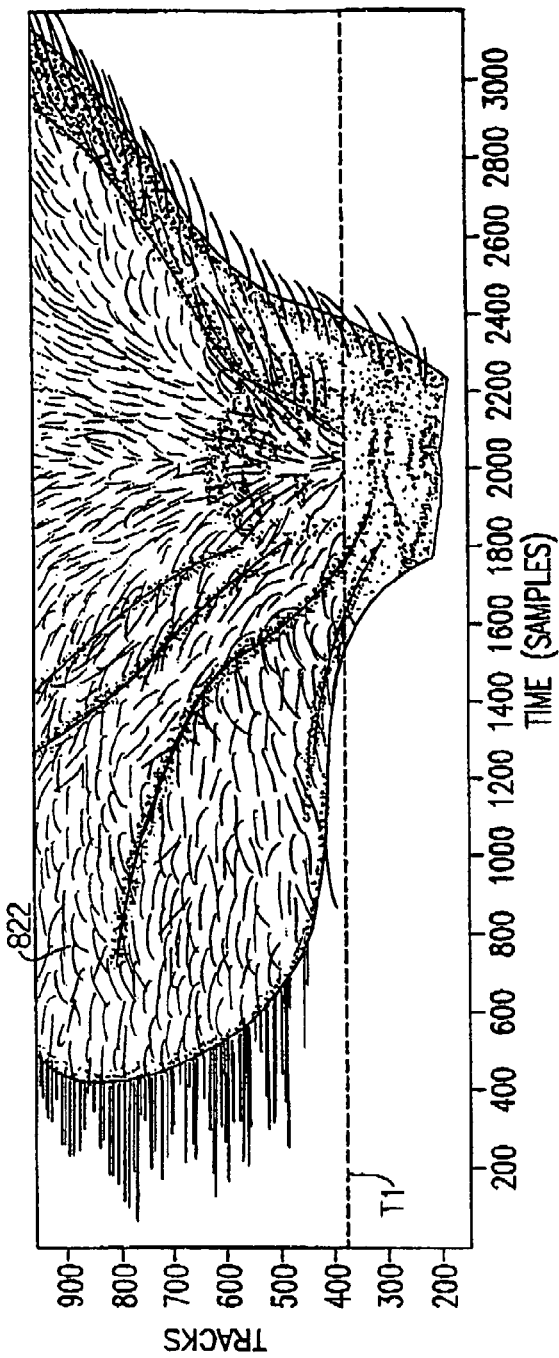
FIG. 13 depicts the position of the gnat wing relative to the tracks of the operational structures.
Figure 14:
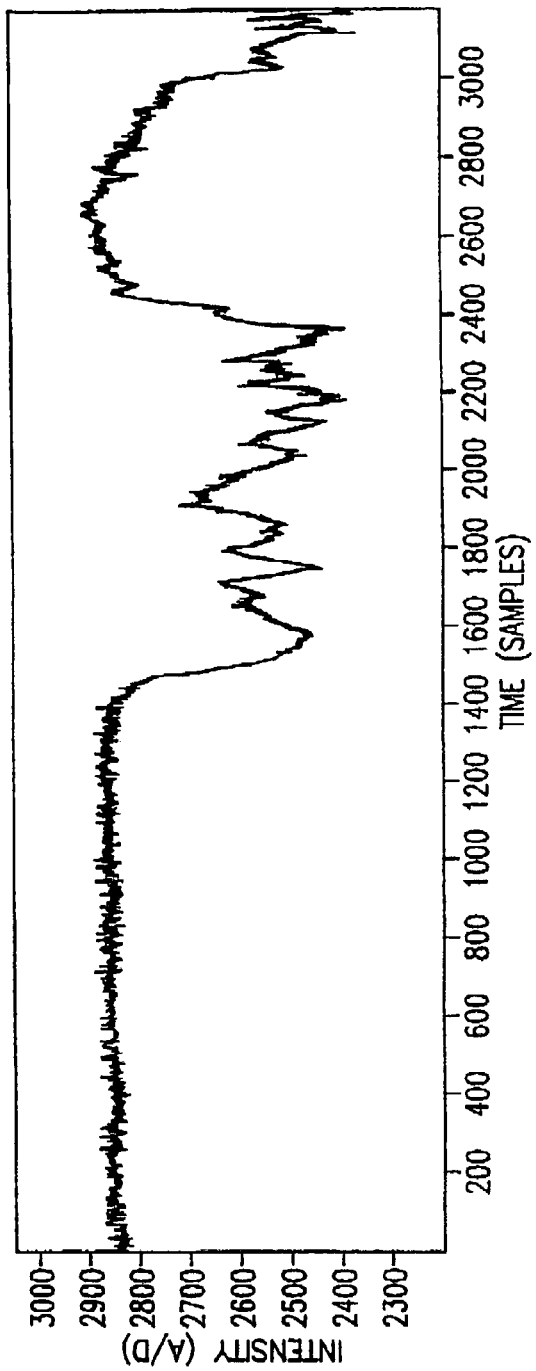
FIG. 14 shows the HF signal acquired from a track depicted in FIG. 13.

FIG. 13 diagrammatically shows the position of the gnat wing 822 relative to the tracks embossed in the operational surface. T1 denotes a track upon which the gnat wing is positioned. FIG. 14 shows the HF signal acquired along the track T1. The HF signal has been digitalized and buffered.

In FIG. 13, the Y-axis, labeled with "TRACKS," represents the number of tracks along a radius of the disc assembly. The X-axis, labeled with "TIME (SAMPLES)," represents the number of sampling along a track. For instance, the gnat wing can be sampled by the disc reader along the track T1 at least about 800 times (from sample number 1550 to sample number 2350).

FIG. 15 shows the position of the gnat wing 822 relative to the tracks T2 and T3. FIG. 16 demonstrates the HF signals for a series of consecutive tracks between T2 and T3.

FIG. 18 is a high density compilation of the HF signals for the tracks across the gnat wing. The image of the gnat wing appears in FIG. 18. FIG. 17 shows the position of the gnat wing 822 relative to the tracks.

Although FIGS. 12 through 18 use an optical disc having only one operational layer, it would be apparent to one of skill in the art that the same principle can be applied to an optical disc having at least two operational layers. For instance, the layer 812 may be a data layer containing optically readable data at its laser-proximal surface.

In accordance with another aspect of the present invention, the optical disc reader includes an objective lens focusing mechanism that is capable of focusing the disc reader's laser onto different surfaces in the disc assembly. FIG. 19 shows a focusing servo 290 that includes a coil and magnet casing surrounding the objective lens. The objective lens 292 directs the laser 294 onto the surface 296 of the disc. Then the laser light travels through a lens layer, and focuses onto the operational surface 298. The operational surface includes operational structures, such as wobble grooves, or pits and lands. The objective lens is held by a brace 302 which is part of the moving coil controlled by the magnet 306. The magnet 306 is activated by the signal generated when the laser light 294 returns from the disc to the detector of the disc reader. The moving coil 304 and the objective lens can move within the range 308. The range 308 controls the range of the laser's focal zone.

As used herein, a laser's focal zone refers to the range of distance within which the laser's focal point may be positioned. In a standard CD drive, the laser's focal zone is about 25 to 26 micrometers. Thus, the laser's focal point can move above and below a trackable surface in a range of about 12.5 to 13 micrometers. Some variations (about ±2 micrometers) are allowed for the movement. Accordingly, an analyte preferably is positioned within about 15 micrometers from the trackable surface in order for the reading beam of an optical disc reader to be focused on the analyte. When a hologram is used to encode operational structures, the analyte preferably is located within about 15 micrometers from the image plane of the hologram. In one embodiment, a surface of the analyte section is located within about 15 micrometers from the trackable surface or the image plane of the hologram. The surface of the analyte section may also be capable of receiving the analyte. The surface of the analyte section may be part of a larger surface of the analyte section. The 15 micrometers limitation may be modified in a modified optical disc reader.

When a DVD reader reads a DVD disc, the focal point of the laser beam can move from one data layer to the other data layer. The two data layers in a DVD disc are about 40 to 70 micrometers apart. Therefore, a DVD reader may allow the focus of the laser beam to move within a range of at least 40 to 70 micrometers. This range may be changed in a modified optical disc reader. The movement of the focal point from one data layer to the other can be regulated by a logic switch encoded in the DVD disc. Together with the 25 to 26 micrometers allowed by the focusing servo, the focal point of the laser beam in a DVD reader can move within a range of about 85 micrometers (i.e. 70 micrometers plus 15 micrometers). Therefore, the analyte of interest can be positioned about 85 micrometers from one of the two operational surfaces of a DVD disc.

With reference again to FIG. 6, there is illustrated a focal zone in a DVD-type disc. The laser's focal point can move in the direction 446 between the planes 448 and 450. The laser may focus on the semi-reflective, semi-transmissive layer 438, or on the reflective layer 440, or on the analytes 444 that is located between the layer 438 and the layer 440. The laser's focal zone encompasses the area between the planes 448 and 450.

The focusing servo of the present invention may move the laser's focal point across the laser's focal zone. The laser's focal point may represent the point where the focusing servo finds a maximal amount of light returned to the disc reader's detector. The location of the laser's focal point therefore may be affected by the reflective properties and other optical properties of various elements included in the optical disc assembly. The focusing servo may be able to search for a focal point from which the light returned to the detector is maximal.

The present invention contemplates a variety of embodiments of the optical disc assembly. For instance, the optical disc can have more than two reflective layers. The operational structures can include pits, lands, grooves, wobble grooves, dye marks, chevron marks, or any combination thereof. The operational structures may act as phase components or create interference patterns that provide tracking and synchronization information to the disc drive. The operational structures can be in a CD format (including a CD-R and CD-RW format), a DVD format (including a DVD-R format, a DVD-RW format, and a DVD-RAM format), or any combination thereof. The operational structures can be physically imprinted in a surface of the operational layer, or encoded in a hologram. A custom format for operational structures may also be used, and the disc assembly is read by a custom decoding device. Different surfaces in the optical disc assembly can be metalized or coated with materials with a variety of reflective properties. The coatings may be reflective, semi-reflective, transmissive, semi-transmissive, or anti-reflective. The materials used in the various layers may be dielectric or non-dielectric. Moreover, the operational layer may be created using different processes, such as molding, electroforming, or web manufacturing.

In one embodiment, the operational structures in the optical disc assembly are designed to provide an improved detection for the investigational structures. The investigational structures may be cells, microorganisms, or any other biological, chemical, or biochemical specimens. In one instance, the pits, lands, or wobble grooves are reconfigured to enhance tangential resolution. In another case, the pits are shortened or the wobble is changed to provide a lower scanning speed in order to increase the radial resolution.

In a preferred embodiment, the operational structures in the optical disc assembly are configured and organized in accordance with the "zoned constant linear velocity" (ZCLV) format. The ZCLV format is detailed in various industry standards, including the DVD-RAM specification. FIG. 20 schematically illustrates the ZCLV format in a circular disc. The ZCLV disc in FIG. 20 is divided into multiple zones 490 across the range 492. Although only five zones are shown in FIG. 20, actual ZCLV format discs may have different numbers of zones. For instance, the DVD-RAM ZCLV format allows 24 zones.

Each of the zones 490 is divided into multiple sectors 494. Inner zones have fewer sectors than outer zones, because the radii of inner zones are less than the radii of outer zones. The optical disc reader can scan each zone at a constant rate. In addition, the optical disc reader can rotate the ZCLV disc faster when it scans the inner zones than when it scans the outer zone. Therefore, the optical disc reader may maintain a substantially constant scanning rate for all the zones in a ZCLV disc.

FIG. 21 shows an enlarged perspective view of a portion of one of the sectors of the ZCLV disc. The operational structures consist of multiple tracks 498 that are arranged radially within the sector. Each track has header information embossed in a "pre-groove" area 500. The pre-groove area is followed by a "wobbled land and groove" area 504 which includes the wobble groove 498 and the wobbled land 502. Operational structures in a ZCLV format may be holographically encoded in a hologram according to the present invention.

FIG. 22 shows a ZCLV-formatted optical disc assembly associated with analytes or investigational structures 510. Analytes or investigational structures 510 may be deposited within the "wobbled land and groove" area 508. The embossed header information in the pre-groove area 506 can be used to store information for identifying or controlling a desired measurement of the analytes or investigational structures 510. Accordingly, different sectors in the same ZCLV disc may be used to perform different measurements or assays.

In one embodiment, the zones in a ZCLV formatted disc can be mastered in such a way as to provide either a highly reflective surface, a partly reflective surface, or a non-reflective surface. In each case, the pre-header information can provide tracking and location information. The pre-header information may also provide identification information for the nature of the zone. In addition, the pre-header information may encode information relating to the software or firmware that is applied to the zone. The characteristics of the investigational structures (such as their reflectivity, absorptivity, or transmissivity) can be determined by the disc laser as it scans over each zone. Information that controls the measurement of investigational structures is encoded or embossed in the pre-groove areas.

In one embodiment, the analyte section of the optical disc assembly can be configured to receive an insert that holds the analyte of interest. The insert can be glass or plastic. The insert may be a sample slide regularly used for examining biological, chemical, or biochemical samples. The insert may be replaceable or integrated with the disc assembly. The insert may hold chemical, biological, biochemical, or other physical specimens. Chemical, biochemical, or biological reactions, including molecule-molecule bindings or enzymatic reactions, can be performed either on the insert or in the analyte section. Products and/or by-products of these chemical, biochemical, or biological reactions may generate optical effects on the incident laser light that can in turn be detected by the disc reader. The insert may function as a cover layer or a lens layer.

The analyte section may include investigational structures that are replaceable or integrated with the disc assembly. The investigational structures or features may include light absorbing, light reflecting, or anti-reflective materials, so that they may be detectable by the optical pickup of the disc reader. The focusing servo may search for the focal point with maximal return light. Such a focal point may depend on the reflectivity of the investigational structures.

In another embodiment, the optical disc assembly may include channels, including microfluidic channels, or chambers. These channels or chambers are capable of transporting analytes, reactive components or mediums to and from the analyte section. Analytes and other components can be mixed within these channels or chambers. Preferably, the analyte section also includes at least one chamber or channel that is capable of holding the analytes for investigation. The operational surface may include a cut-away area or window which may be either laser-proximal or laser-distal to the analyte section and which may be adjacent to the analyte section. The analyte section may include or be adjacent to a cut-away area or window.

FIG. 23 illustrates an example of a dual data layer disc assembly. The operational layer 702 includes operational structures 700 at its laser-distal surface. The operational structures 700 may be coated with a reflective or semi-reflective layer. The cover layer 706 is affixed to the operational layer 702 through an adhesive layer 708. The insert layer 710 includes operational structures 712 at its laser-proximal surface. The insert layer 710 can be placed into a space within the cover layer 706. The operational structures 712 are coated with a reflective layer 714. The chamber 704 is located between the insert layer 710 and the operational layer 702. Analytes or investigational structures 720 can be placed in the chamber 704. Reaction medium or other material may be introduced into the chamber 704 through fluidic channels 722. Chemical, biochemical, or biological reactions, which produce detectable optical signals, may be carried out in the chamber 704. The laser 716 can be focused within the full range of its focal zone 718. In this embodiment, the chamber 704 includes a cut-away area or window in the operational surface of the layer 702.

FIG. 24 illustrates another example of a dual data layer disc assembly according to the present invention. The operational structures at the laser-distal surface of the first operational layer 794 are coated with a reflective layer 790, which preferably is semi-reflective and semi-transmissive. The operational structures at the laser-proximal surface of the second operational layer 772 are coated with a reflective layer 782. The second operational layer 772 has a sample entry port 774 and a micro-fluidic circuit 776. A valve 780 is present before the circuit 776 connects to another micro-fluidic circuit 786. The micro-fluidic circuit 786 is located in the space layer 784 which contains adhesive material that binds the first and the second operational layers together. The focal zone 792 encompasses the operational surfaces of the first and the second operational layers 772 and 794. The focal zone 792 also includes the space layer 784.

The operational surface of the operational layer 794 has a cut-away area or window. The laser beam can pass through the cut-away area or window to enter the micro-fluidic circuit 786. In one embodiment, the space layer 784 may further include an area for colorimetric assay, or an area for cell capture assay. In another embodiment, the operational surfaces of the layer 794 and/or the layer 772 may have encoded data that controls assays on the analytes. Data relating to the control of the valve may also be encoded in the operational surfaces.

In a preferred embodiment, one of the operational layers in a multiple data layer disc is a hologram. Operational structures are encoded in the hologram. Preferably, the hologram is a reflective hologram, and is protected by a transparent protective coating located laser-proximal to the hologram. FIG. 25 shows an optical disc assembly including a reflective hologram 512 that is protected by a transparent protective coating 514. The hologram encodes the operational structures, such as wobble grooves, that are required by the operation of the optical disc reader. When a laser beam 516 is reflected from the hologram physical plane 512, it appears as though the encoded operational structures, such as wobble grooves in a correct orientation, are present at the hologram image plane 518. The hologram image plane 518 can be located substantially confocal with the investigational structure 520. The investigational structure 520 may be positioned on the semi-reflective layer 522 that coats the operational surface of the data layer 524.

The laser beam may be focused on the image plane 518 that may be shared by both the investigational structure 520 and the encoded operational structures. Therefore, light from the image plane 518 may enable the disc reader to generate both the operational signals, such as the signals used for disc tracking, and the investigational signals that are indicative of the presence of the investigational structure. This feature allows the optical disc reader to track the disc and detect the investigational structure concurrently and discriminably. The larger the illuminating laser spot 526 on the hologram, the better the image of the operational structures as appeared in the image plane 518. Therefore, the laser preferably is not tightly focused on the hologram physical plane. Typically, a portion of the hologram physical surface may be sufficient to generate the entirety of the image of the operational structures that are interferometrically encoded in the hologram.

An investigational structure can be positioned non-concurrently with the image plane of the hologram, provided that the operational structures, such as the wobble groove, can be concurrently detectable with the investigational structure. The image plane of the hologram may be either laser-proximal or laser-distal to the investigational structure. The investigational structure may be located between the image plane of the hologram and the data layer 524. The investigational structure may be located on the physical plane of the hologram. The investigational structure may be located on the semi-reflective layer 522, or laser-proximal thereto. In addition, the hologram image plane may be either laser-proximal or laser-distal to the hologram's physical plane.

Preferably, the hologram is replaceable or reversibly attachable to the disc assembly. This permits the hologram to be mass-produced using a high-speed holographic printing process. This also permits the re-use of the hologram or other parts of the disc assembly.

In addition to the above-described features, many other features of multiple data layer discs are contemplated by this invention. For instance, chambers or channels that are capable of holding analytes may be located in various places in a multiple data layer disc. As shown in FIG. 26, the analyte channel 571 is located within the laser-distal operational layer 572. The analyte channels 574 and 575 are located between the two operational layers. The analyte channel 574 is located closer to the operational layer 577 than to the analyte channel 575. The analyte channel 573 is located within the operational layer 573. Analytes in these channels may be detectable by the optical disc reader. Channels 576 and 577 may allow analytes or other components to enter or exit the analyte channels. The analytes in these channels preferably are located with the focal zone of the reading beam in order to be focused thereupon. Preferably, at least part of each analyte channel is within 15 micrometers from at least one of the two operational surfaces in the disc.

In one embodiment, the laser-distal operational layer may include a cut-away area or window. The reading beam of the optical disc reader may pass through the cut-away area or window to reach a top detector. Analytes that are disposed in the optical disc may be detected by a top detector. FIG. 27 depicts an example of this embodiment. The operational surface of the laser-proximal operational layer 610 is coated with a semi-reflective layer 614. The operational surface of the laser-distal operational layer 612 is coated with a second reflective layer 616 which may be highly reflective. The reading beam 628 may be focused on either the semi-reflective layer 614, the analyte 624, or the reflective layer 616. Light reflected from the semi-reflective layer 614, the analyte 624, or the reflective layer 616 may be acquired by a bottom detector of the optical disc reader to generate operational signals or investigational signals. The reflective layer 616 may also be semi-reflective so that the reading beam may pass through the optical disc to reach a top detector 636 of the optical disc reader.

The operational surface in the laser-distal operational layer 612 may have a cut-away area or window 626. Analytes, such as the analyte 620, may be placed laser-proximal to the cut-away area or window. The reading beam

630 may be focused on the semi-reflective layer 614 or the analyte 620. Light returned from the semi-reflective layer 614 may provide operational signals. The reading beam 630 can pass through the cut-away area or window 626 and reach the top detector 636 of the optical disc reader. The analyte 620 may modulate the pass-through reading beam, and therefore enable the top detector 636 to generate signals indicative of the presence of the analyte 620 in the optical disc. As would be appreciated by those of skill in the art, the optical disc shown in FIG. 27, as well as other dual data layer optical discs described in this invention, may be modified to have more than two data or operational layers.

In another embodiment, the disc is a hybrid disc in that the operational surface includes at least two different formats of operational structures. For instance, the operational surface may include both operational structures in a CD format and operational structures in a DVD format. The disc reader may read both formats. Data facilitating or regulating the disc reader to read different formats of operational structures may be encoded or embossed in the disc.

In yet another embodiment, data other than operational structures can be encoded or embossed in the operational surface or other data surfaces in the disc assembly. These data may provide control information for the disc reader to read or detect the investigational structures. These data may regulate the measurement of investigational structures, for instance, by controlling valves that can manage fluidic flows in a fluidic circuit. These data, as well as the operational structures or other information, may be written to the disc before, during, or after the investigational structures are read or detected.

The disc assembly may be used for detecting biological suspensions such as blood, urine, saliva, amniotic fluid, cerebrospinal fluid, synovial fluid, pleural fluid, pericardial fluid, perintoneal fluid. Environmental and chemical samples may also be assayed using the disc assembly. The disc assembly may include embossed features, placed features, or etched features.

The disc assembly may be a null type disc, a modified disc based on industry standard disc, or a disc based on a custom format. Preferably, the disc assembly does not have a dye layer.

The multiple operational layer format supports the measurement of high-density investigational structures. The multiple operational layer format also supports the creation of high-density structures, such as micro-fluidic circuits, that are configured to receive and hold investigational structures. The laser's focus can switch between different operational layers. The switch may be controlled by the logical information encoded in the operational surfaces of the operational layers. The encoded logical information may control valves that regulate fluidic flows in a circuit, such as a micro-fluidic circuit.

The DVD format may allow a DVD drive to reprogram itself from information encoded or embossed in a DVD disc being read. This provides a means for reprogramming a DVD drive in order to perform any special processing required to detect the presence of the investigational structures. Program codes can be encoded in the operational surface or any other surfaces in a DVD disc.

The investigational structures can be phase components or cause light cancellation. The investigational structures may be highly reflective, semi-reflective, or non-reflective. The reflectivity of the investigational structures may also be changed by chemical, biochemical, or biological reactions designed to be carried out in the disc assembly. The laser can be focused on a plane with a reflectivity that may vary in a broad range, therefore providing contrast for the investigational structures.

The multiple data layer disc design provides a higher mechanical and optical resolution for the detections of the investigational structures that are disposed in the disc assembly. For instance, the analyte resolution in a DVD-based disc is usually higher than the analyte resolution in a CD-based disc. This may be attributed to the shorter wavelength of the laser used in a DVD reader.

In one embodiment, a DVD-based optical disc assembly has zones that are free of operational structures. The zones may be located in the operational surfaces. The zones may have a highly reflective surface to provide a contrast for a non-reflective investigational structure. The zones may also have a partially reflective surface to provide a contrast for a reflective investigational structure. The zones may provide physical support for the investigational structures. The laser may be focused on the zones, and the investigational structures may become excited by the laser to emit measurable signals. In one case, the investigational structures can create phase cancellation responses.

It should be understood that the above-described embodiments are given by way of illustration, not limitation. Various changes and modifications within the spirit and scope of the present invention will become apparent to those skilled in the art from the above description. In addition, the reader's attention is directed to the provisional applications from which the present application claims the benefit of priority. The contents of all these provisional applications are incorporated herein by reference.

What is claimed is:

1. An optical disc, comprising:
    a first layer including optically readable structures which have encoded tracking information;
    a second layer including optically readable structures; and
    an analyte section capable of receiving an analyte which can be read by an optical disc reader.

2. The optical disc according to claim 1 wherein the analyte section includes a first chamber, and at least part of the first chamber is within the optical disc.

3. The optical disc according to claim 2 wherein at least one of the first layer and the second layer contains a first channel connecting to the first chamber.

4. The optical disk according to claim 3 wherein the optical disc reader is a DVD reader or a CD reader.

5. The optical disc according to claim 3 wherein the first channel includes a valve which can be regulated by optically readable data encoded in the optical disc.

6. The optical disc according to claim 3 wherein the analyte section includes a second chamber, at least part of the second chamber being located within the optical disc, and at least one of the first layer and the second layer containing a second channel connecting to the second chamber.

7. The optical disc according to claim 2 wherein said optically readable structures in the first layer are impressed in a surface of the first layer and are coated with a first reflective layer, and said optically readable structures in the second layer are impressed in a surface of the second layer and are coated with a second reflective layer, the first reflective layer and the second reflective layer being located between the first layer and the second layer.

8. The optical disc according to claim 7 wherein the second reflective layer is semi-reflective.

9. The optical disc according to claim 7 wherein the first reflective surface is semi-reflective.

10. The optical disc according to claim 9 wherein said surface of the first chamber holds the analyte.

11. The optical disc according to claim 7 wherein at least one of said surface of the first layer and said surface of the second layer includes an area which lacks optical readable structures that have encoded tracking information, and a surface of the first chamber includes said area.

12. The optical disc according to claim 7 wherein at least one of said surface of the first layer and said surface of the second layer includes an area which lacks reflective coatings, and a surface of the first chamber includes said area.

13. The optical disc according to claim 7 wherein said optically readable structures in the first layer or said optically readable structures in the second layer have encoded assay information for conducting an assay on the analyte.

14. The optical disc according to claim 13 wherein said optically readable structures in the first layer or said optically readable structures in the second layer have encoded focus control information enabling the optical disc reader to move the focal point of a reading beam in a manner determinable from said focus control information.

15. The optical disc according to claim 1 wherein at least one of the first layer and the second layer is a hologram.

16. The optical disc according to claim 15 wherein the optical disc reader is a CD or DVD reader.

17. The optical disc according to claim 15 wherein at least part of an image plane of the hologram is located with the analyte section.

18. The optical disc according to claim 15 wherein the analyte section includes a surface which is located within 15 micrometers from the image plane of the hologram.

19. The optical disc according to claim 18 wherein said surface of the analyte section is within the image plane of the hologram.

20. The optical disc according to claim 18 wherein said surface of the analyte section holds the analyte.

21. An optical disc, comprising:
a first layer including optically readable structures which have encoded information enabling an optical disc reader to cause rotation of the optical disc in a manner that is determinable from said information;
a second layer including optically readable structures; and
an analyte section capable of receiving an analyte which can be read by the optical disc reader.

22. The optical disc according to claim 21 wherein the analyte section includes a first chamber, and at least part of the first chamber is within the optical disc.

23. The optical disc according to claim 22 wherein at least one of the first layer and the second layer contains a first channel connecting to the first chamber.

24. The optical disk according to claim 23 wherein the optical disc reader is a DVD reader or a CD reader.

25. The optical disc according to claim 23 wherein the first channel includes a valve which can be regulated by optically readable data encoded in the optical disc.

26. The optical disc according to claim 23 wherein the analyte section includes a second chamber, at least part of the second chamber being located within the optical disc, and at least one of the first layer and the second layer containing a second channel connecting to the second chamber.

27. The optical disc according to claim 22 wherein said optically readable structures in the first layer are impressed in a surface of the first layer and are coated with a first reflective layer, and said optically readable structures in the second layer are impressed in a surface of the second layer and are coated with a second reflective layer, the first reflective layer and the second reflective layer being located between the first layer and the second layer.

28. The optical disc according to claim 27 wherein at least one of said surface of the first layer and said surface of the second layer includes an area which lacks optical readable structures that have encoded tracking information, and a surface of the first chamber includes said area.

29. The optical disc according to claim 27 wherein at least one of said surface of the first layer and said surface of the second layer includes an area which lacks reflective coatings, and a surface of the first chamber includes said area.

30. The optical disc according to claim 27 wherein said optically readable structures in the first layer or said optically readable structures in the second layer have encoded assay information for conducting an assay on the analyte.

31. The optical disc according to claim 21 wherein at least one of the first layer and the second layer is a hologram.

32. A method for detecting an analyte held in the analyte section of the optical disc of claim 21, comprising:
providing the optical disc to the optical disc reader;
reading the optical disc; and
obtaining at least one signal which is indicative of the presence of the analyte.

33. The method according to claim 32 wherein the optical disc reader includes at least two detectors, one detector being capable of generating tracking signals, and the other detector being capable of receiving radiation that passes through the optical disc and generating said signal which is indicative of the presence of the analyte.

34. An optical disc, comprising:
optically readable structures which have encoded information enabling an optical disc reader to cause rotation of the optical disc in a manner that is determinable from said information; and
an analyte section capable of receiving an analyte which can be read by the optical disc reader.

* * * * *